(12) United States Patent  (10) Patent No.: US 9,015,803 B1
Chaganti et al.  (45) Date of Patent: *Apr. 21, 2015

(54) ONLINE PERSONAL LIBRARY

(71) Applicant: Pennar Software Corporation, Alexandria, VA (US)

(72) Inventors: Naren Chaganti, Town and Country, MO (US); Sitapathi Rao Chaganti, Nellore (IN); Damayanti Chaganti, Nellore (IN)

(73) Assignee: Pennar Software Coporation, Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/076,192

(22) Filed: Nov. 9, 2013

Related U.S. Application Data

(63) Continuation of application No. 09/634,725, filed on Aug. 5, 2000, and a continuation-in-part of application No. 09/478,796, filed on Jan. 7, 2000, now Pat. No. 6,845,448.

(51) Int. Cl.
*H04L 29/06* (2006.01)

(52) U.S. Cl.
CPC .............. *H04L 63/10* (2013.01); *H04L 63/105* (2013.01)

(58) Field of Classification Search
None
See application file for complete search history.

(56) References Cited

U.S. PATENT DOCUMENTS

| | | |
|---|---|---|
| RE31,302 E | 7/1983 | Stambler |
| 4,956,769 A | 9/1990 | Smith |
| 5,144,557 A | 9/1992 | Wang et al. |
| 5,204,897 A | 4/1993 | Wyman |
| 5,241,466 A | 8/1993 | Perry |
| 5,247,672 A | 9/1993 | Mohan |
| 5,267,314 A | 11/1993 | Stambler |
| 5,276,901 A | 1/1994 | Howell |
| 5,355,474 A | 10/1994 | Thuraisngham |
| 5,428,778 A | 6/1995 | Brookes |
| 5,475,839 A | 12/1995 | Watson |
| 5,510,777 A | 4/1996 | Pilc |
| 5,524,073 A | 6/1996 | Stambler |
| 5,555,303 A | 9/1996 | Stambler |
| 5,608,874 A | 3/1997 | Ogawa |
| 5,621,727 A | 4/1997 | Vaudreuil |
| 5,644,711 A | 7/1997 | Murphy |
| 5,646,998 A | 7/1997 | Stambler |

(Continued)

OTHER PUBLICATIONS

Chuck Moozakis "Internet Printing Takes Hold" dated Sep. 29, 1998, online article, Retrieved from the Internet on Aug. 10, 2000, URL:http://www.internetwork.com/news0998/news092998-1.htm.

(Continued)

*Primary Examiner* — Benjamin Lanier

(57) ABSTRACT

In a server-computer implemented system for online document collaboration, a document stored online in a first account may be modified by one or more of an authorized first group of users, which modifications are received and applied to the document. Electronic notification that the document is modified is sent to one or more of an authorized second group of users, who can thereafter further modify the document, or indicate their approval or disapproval of the modifications made by the one or more of the authorized first group of users. The one or more of the authorized first group of users is authorized to make specific permitted changes to the document, and if an attempt is made to change the document in a manner not permitted, then an alarm condition is generated.

106 Claims, 8 Drawing Sheets

(56) References Cited

U.S. PATENT DOCUMENTS

| | | | |
|---|---|---|---|
| 5,694,590 A | 12/1997 | Thuraisingham | |
| 5,706,507 A | 1/1998 | Schloss | |
| 5,710,578 A | 1/1998 | Beauregard | |
| 5,761,499 A | 6/1998 | Sonderegger | |
| 5,765,152 A | 6/1998 | Erickson | |
| 5,767,853 A | 6/1998 | Yoshida | |
| 5,790,664 A | 8/1998 | Coley | |
| 5,793,302 A | 8/1998 | Stambler | |
| 5,832,208 A | 11/1998 | Chen | |
| 5,832,508 A | 11/1998 | Sherman | |
| 5,848,426 A | 12/1998 | Wang | |
| 5,870,552 A | 2/1999 | Dozier | |
| 5,931,901 A | 8/1999 | Wolfe | |
| 5,936,541 A | 8/1999 | Stambler | |
| 5,974,148 A | 10/1999 | Stambler | |
| 6,000,033 A | 12/1999 | Kelley | |
| 6,005,939 A | 12/1999 | Fortenberry | |
| 6,041,357 A | 3/2000 | Kunzelman | |
| 6,042,519 A | 3/2000 | Shea | |
| 6,070,185 A | 5/2000 | Anupam | |
| 6,073,106 A | 6/2000 | Rozen | |
| 6,076,109 A | 6/2000 | Kikinis | |
| 6,092,080 A | 7/2000 | Gustman | |
| 6,092,196 A | 7/2000 | Reiche | |
| 6,139,495 A | 10/2000 | De La Huerga | |
| 6,148,342 A | 11/2000 | Ho | |
| 6,161,123 A | 12/2000 | Renouard | |
| 6,161,185 A | 12/2000 | Guthrie | |
| 6,175,831 B1 | 1/2001 | Weinreich | |
| 6,181,803 B1 | 1/2001 | Davis | |
| 6,205,478 B1 | 3/2001 | Sugano | |
| 6,266,649 B1 | 7/2001 | Linden | |
| 6,269,369 B1 | 7/2001 | Robertson | |
| 6,275,937 B1 | 8/2001 | Hailpern | |
| 6,298,446 B1* | 10/2001 | Schreiber et al. | 726/27 |
| 6,311,162 B1 | 10/2001 | Reichwein | |
| 6,321,334 B1 | 11/2001 | Jerger | |
| 6,367,012 B1 | 4/2002 | Atkinson | |
| 6,377,161 B1 | 4/2002 | Gromelski | |
| 6,405,195 B1 | 6/2002 | Ahlberg | |
| 6,453,305 B1 | 9/2002 | Glassman | |
| 6,457,010 B1 | 9/2002 | Eldering | |
| 6,477,580 B1 | 11/2002 | Bowman-Amuah | |
| 6,480,958 B1 | 11/2002 | Harrington | |
| 6,487,552 B1 | 11/2002 | Lei | |
| 6,489,954 B1* | 12/2002 | Powlette | 715/733 |
| 6,496,849 B1 | 12/2002 | Hanson | |
| 6,505,160 B1 | 1/2003 | Levy | |
| 6,507,865 B1 | 1/2003 | Hanson | |
| 6,615,251 B1 | 9/2003 | Klug | |
| 6,662,343 B1 | 12/2003 | Gebauer | |
| 6,687,745 B1 | 2/2004 | Franco | |
| 6,792,458 B1 | 9/2004 | Muret | |
| 6,850,916 B1 | 2/2005 | Wang | |
| 6,882,793 B1 | 4/2005 | Fu | |
| 6,918,082 B1 | 7/2005 | Gross | |
| 7,058,696 B1 | 6/2006 | Phillips | |
| 7,130,807 B1 | 10/2006 | Mikurak | |
| 7,155,737 B1 | 12/2006 | Lim | |
| 7,167,904 B1 | 1/2007 | Devarajan | |
| 7,243,079 B1 | 7/2007 | Manolis | |
| 7,246,069 B1 | 7/2007 | O'Hanlon | |
| 7,353,199 B1 | 4/2008 | DiStefano | |
| 7,599,854 B1 | 10/2009 | Baum | |
| 7,630,986 B1 | 12/2009 | Herz | |
| 2001/0031066 A1 | 10/2001 | Meyer et al. | |
| 2001/0050990 A1 | 12/2001 | Sudia | |
| 2002/0059402 A1 | 5/2002 | Belanger | |
| 2002/0069272 A1 | 6/2002 | Kim | |
| 2002/0174010 A1* | 11/2002 | Rice, III | 705/14 |
| 2003/0055652 A1* | 3/2003 | Nichols et al. | 704/275 |
| 2003/0069874 A1 | 4/2003 | Hertzog | |
| 2004/0021686 A1 | 2/2004 | Barberis | |

OTHER PUBLICATIONS

Rolf Blom, Mats Naslund, Goran Selander, Object Security and Personal Information Management, Apr. 27, 2001.

Kelso, "Final Report on the National Integration Resource Center Task Force—The Lisle Report," Apr. 19, 1999, retrieved on Sep. 14, 2000 from http://www.ojp.usdoj.gov/integratedjustice/hsle-fn.htm.

Kendall, et al., "Privacy Impact Assessment for Justice Information Systems," Working Paper, Draft, Jul. 5, 2000, retrieved on Sep. 14, 2000 from http://www.ojp.usdoj.gov/integratedjustice/piajis.htm, pp. 30-31.

Gardner, "Office of Justice Programs, Integrated Justice Privacy Initiative," Apr. 12, 2000, retrieved on Sep. 14, 2000 from http://www.ojp.usdoj.gov/integratedjustice/bp3.htm.

Cavoukian et al., "Privacy Design Principles for an Integrated Justice System," Working Paper, Apr. 5, 2000, retrieved on Sep. 14, 2000 from http://www.ojp.usdoj.gov/integratedjustice/pdpapril.htm.

J. Michael Murphy, "Privacy Protection—A New Beginning?" 21st International Conference on Privacy and Personal Data Protection, Sep. 13-14, 1999, retrieved on Sep. 14, 2000 from http://www.pco.org.hk/conproceed.html.

Ann Cavoukian, "Privacy and Biometrics," 21st International Conference on Privacy and Personal Data Protection, Sep. 13-14, 1999, retrieved on Sep. 14, 2000 from http://www.pco.org.hk/conproceed.html.

Lorrie Faith Cranor, "Agents of Choice: Tools That Facilitate Notice and Choice About Web Site Data Practices," 21st International Conference on Privacy and Personal Data Protection, Sep. 13-14, 1999, retrieved on Sep. 14, 2000 from http://www.pco.org.hk/conproceed.html.

Austin Hill, "The Privacy Risks of Public Key Infrastructures, 21st International Conference on Privacy and Personal Data Protection", Sep. 13-14, 1999, retrieved on Sep. 14, 2000 from http://www.pco.org.hk/conproceed.html.

Armgard Von Reden, Data Protection Activities in the Private Sector, 21st International Conference on Privacy and Personal Data Protection, Sep. 13-14, 1999, retrieved on Sep. 14, 2000 from http://www.pco.org.hk/conproceed.html.

Nigel Waters, "Re-Thinking Information Privacy—A Third Way in Data Protection?", 21st International Conference on Privacy and Personal Data Protection, Sep. 13-14, 1999, retrieved on Sep. 14, 2000 from http://www.pco.org.hk/conproceed.html.

Hansjuergen Garstka, "The International Working Group on Data Protection in Telecommunications: Common Positions Adopted on Selected Emerging Global Issues," 21st International Conference on Privacy and Personal Data Protection, Sep. 13-14, 1999, retrieved on Sep. 14, 2000 from http://www.pco.org.hk/conproceed.html.

Deborah Hurley, "A Whole World in One Glance: Privacy as a Key Enabler of Individual Participation in Democratic Governance", 21st International Conference on Privacy and Personal Data Protection, Sep. 13-14, 1999, retrieved on Sep. 14, 2000 from http://www.pco.org.hk/conproceed.html.

Robert Gellman, "Public Registers and Privacy: Conflicts with Other Values and Interests," 21st International Conference on Privacy and Personal Data Protection, Sep. 13-14, 1999, retrieved on Sep. 14, 2000 from http://www.pco.org.hk/conproceed.html.

Blair Stewart, "Five Strategies for Addressing Public Register Privacy Problems," 21st International Conference on Privacy and Personal Data Protection, Sep. 13-14, 1999, retrieved on Sep. 14, 2000 from http://www.pco.org.hk/conproceed.html.

David Banisar, "Privacy and Data Protection Around the World," 21st International Conference on Privacy and Personal Data Protection, Sep. 13-14, 1999, retrieved on Sep. 14, 2000 from http://www.pco.org.hk/conproceed.html.

Alfred Bullesbach, "Data Protection and Privacy at a Global Enterprise," 21st International Conference on Privacy and Personal Data Protection, Sep. 13-14, 1999, retrieved on Sep. 14, 2000 from http://www.pco.org.hk/conproceed.html.

Anne Carblanc, "Activities of the OECD—1997-2000—Global Privacy Protection Builds Trust in Electronic Commerce Global Networks", 21st International Conference on Privacy and Personal Data Protection, Sep. 13-14, 1999, retrieved on Sep. 14, 2000 from http://www.pco.org.hk/conproceed.html.

(56) References Cited

OTHER PUBLICATIONS

Philip E. Agre, "Imagining Surveillance: Notes on 1984 and Enemy of the State," 21st International Conference on Privacy and Personal Data Protection, Sep. 13-14, 1999, retrieved on Sep. 14, 2000 from http://www.pco.org.hk/conproceed.html.
Roger Clarke, "Person-Location and Person-Tracking: Technologies, Risks and Policy Implications," 21st International Conference on Privacy and Personal Data Protection, Sep. 13-14, 1999, retrieved on Sep. 14, 2000 from http://www.pco.org.hk/conproceed.html.
Simon Davies, "Big Brother at the Box Office—Electronic Visual Surveillance and the Big Screen," 21st International Conference on Privacy and Personal Data Protection, Sep. 13-14, 1999, retrieved on Sep. 14, 2000 from http://www.pco.org.hk/conproceed.html.
Paul F. Kendall, "Gathering, Analysis and Sharing of Criminal Justice Information by Justice Agenices: The Need for Principles of Responsible Use," 21st International Conference on Privacy and Personal Data Protection, Sep. 13-14, 1999, retrieved on Sep. 14, 2000 from http://www.pco.org.hk/conproceed.html.
Souheil El Zein, "Reconciling Data Protection Regulations with the Requirements of Judicial and Police Co-operation," 21st International Conference on Privacy and Personal Data Protection, Sep. 13-14, 1999, retrieved on Sep. 14, 2000 from http://www.pco.org.hk/conproceed.html.
Bart De Schutter, International Police Co-operation and Privacy Protection, 21st International Conference on Privacy and Personal Data Protection, Sep. 13-14, 1999, retrieved on Sep. 14, 2000 from http://www.pco.org.hk/conproceed.html.
David H. Flaherty, "Balancing Open Government and Privacy Protection," 21st International Conference on Privacy and Personal Data Protection, Sep. 13-14, 1999, rerieved on Sep. 14, 2000 from http://www.pco.org.hk/conproceed.html.
Michel Gentot, "Access to Information and Protection of Personal Data," 21st International Conference on Privacy and Personal Data Protection, Sep. 13-14, 1999, retrieved on Sep. 14, 2000 from http://www.pco.org.hk/conproceed. html.
Bruno Baeriswyl and Peter Heinzmann, "Privacy Audits with External Experts—Cooperation or Attack?", 21st International Conference on Privacy and Personal Data Protection, Sep. 13-14, 1999, retrieved on Sep. 14, 2000 from http://www.pco.org.hk/conproceed.html.
Stephen Wolley, "Data Security and Privacy Audits Adding Value to the Organisation," 21st—International Conference on Privacy and Personal Data Protection, Sep. 13-14, 1999, retrieved on Sep. 14, 2000 from http://www.pco.org.hk/conproceed.html.
David Flaherty, "How to Do a Privacy and Freedom of Information Act Site Visit," 21st International Conference on Privacy and Personal Data Protection, Sep. 13-14, 1999, retrieved on Sep. 14, 2000 from http://www.pco.org.hk/conproceed.html.
Jane Elizabeth Kirtley, "Privacy and the News Media—A Question of Trust, or of Control'?," 21st International Conference on Privacy and Personal Data Protection, Sep. 13-14, 1999, retrieved on Sep. 14, 2000 from http://www.pco.org.hk/conproceed.html.
Raymond Wacks, "Privacy Reconceived: Personal Information and Free Speech," 21st International Conference on Privacy and Personal Data Protection, Sep. 13-14, 1999, retrieved on Sep. 14, 2000 from http://www.pco.org.hk/conproceed.html.
Pamela W.S. Chan, "Consumer Rights and Electronic Commerce," 21st International Conference on Privacy and Personal Data Protection, Sep. 13-14, 1999, retrieved on Sep. 14, 2000 from http://www.pco.org.hk/conproceed.html.
Alan Westin, "Consumers, E-Commerce, and Privacy: US, UK and Germany," 21st International Conference on Privacy and Personal Data Protection, Sep. 13-14, 1999, retrieved on Sep. 14, 2000 from http://www.pco.org.hk/conproceed.html.
Jon Bing, "Data Protection, Jurisdiction and the Choice of Law," 21st International Conference on Privacy and Personal Data Protection, Sep. 13-14, 1999, retrieved on Sep. 14, 2000 from http://www.pco.org.hk/conproceed.html.
Graham Greenleaf, "'IP, Phone-Home' ECMS, ©-tech, and Protecting Privacy Against Surveillance by Digital Works," 21st International Conference on Privacy and Personal Data Protection, Sep. 13-14, 1999, retrieved on Sep. 14, 2000 from http://www.pco.org.hk/conproceed.html.
Privacy Commissioner's Office—What's New, retrieved on Sep. 14, 2000 from http://www.pco.org.hk/old_press.html, pp. 1-3.
Naren Chaganti, "Integrating Electronic Message Handling Systems with Databases: A Security Perspective", Masters Thesis, May 1992, The University of Texas at Arlington, Arlington, TX.
3Com, "ReachOut Remote Control Host User's Guide", Jun. 1996, 3Com, pp. 1-63.
3Com, "ReachOut Remote Control Viewer User's Guide", May 1996, 3Com, pp. 1-57.
P R Newswire, "STAC's New ReachOut 6.0 for Windows 95 Delivers Worldwide Web Browser Access to Your Desktop Files," 0612411 996, PR Newswire Association, Inc., p624LAM022.
"Sixdegrees—About Privacy"—from http://www.sixdegrees.com/about/privacy.html dated Apr. 1998, pp. 1-3.
http://www.freeservers.com, Apr. 29, 1999, pp. 1-3.

\* cited by examiner

| NAME OF THE LIBRARY | _____ ~402 |

| OVERALL SECURITY LEVEL | _____ ~404 |
| | (DEFAULT - 0) |

TYPE OF FILE
- ◇ FORMATTED TEXT (WORD)
- ◇ ASCII TEXT ~406
- ◇ HTML
- ◇ RTF
- ◇ JPEG
- ◇ MPEG
- ○
- ○
- ○

| AUTHOR | _____ |
| FILE NAME | _____ |

PERMISSION TO USERS ~408

AT SECURITY LEVEL [___]  ◇ READ  ◇ WRITE

AT SECURITY LEVEL [___]  ◇ READ  ◇ WRITE

◇ DELETE  ◇ EDIT

CREATING SPACE IN LIBRARY WITH SECURITY LEVELS ~400
AND PERMISSIONS

FIG. 4

SOURCE : http://www.source.com/1/2/b/Movie.mpg

DESTINATION : www.library.com/username/account_id

Destination Password: ADD THIS ONE

| | |
|---|---|
| NAME OF THE LIBRARY | |
| SECURITY LEVEL | |

FILE TYPE   ◇ FORMATTED TEXT (WORD)   ◇ ASCII TEXT   ◇ HTML   ◇ RTF   ◇ JPEG   ◆ MPEG

| | |
|---|---|
| AUTHOR | |
| FILE NAME | |
| ISBN NO.: | |

USER PERMISSIONS (DEFAULT)

CONTENTS OF A REQUEST TO ADD AN ITEM TO A USER LIBRARY

FIG. 5

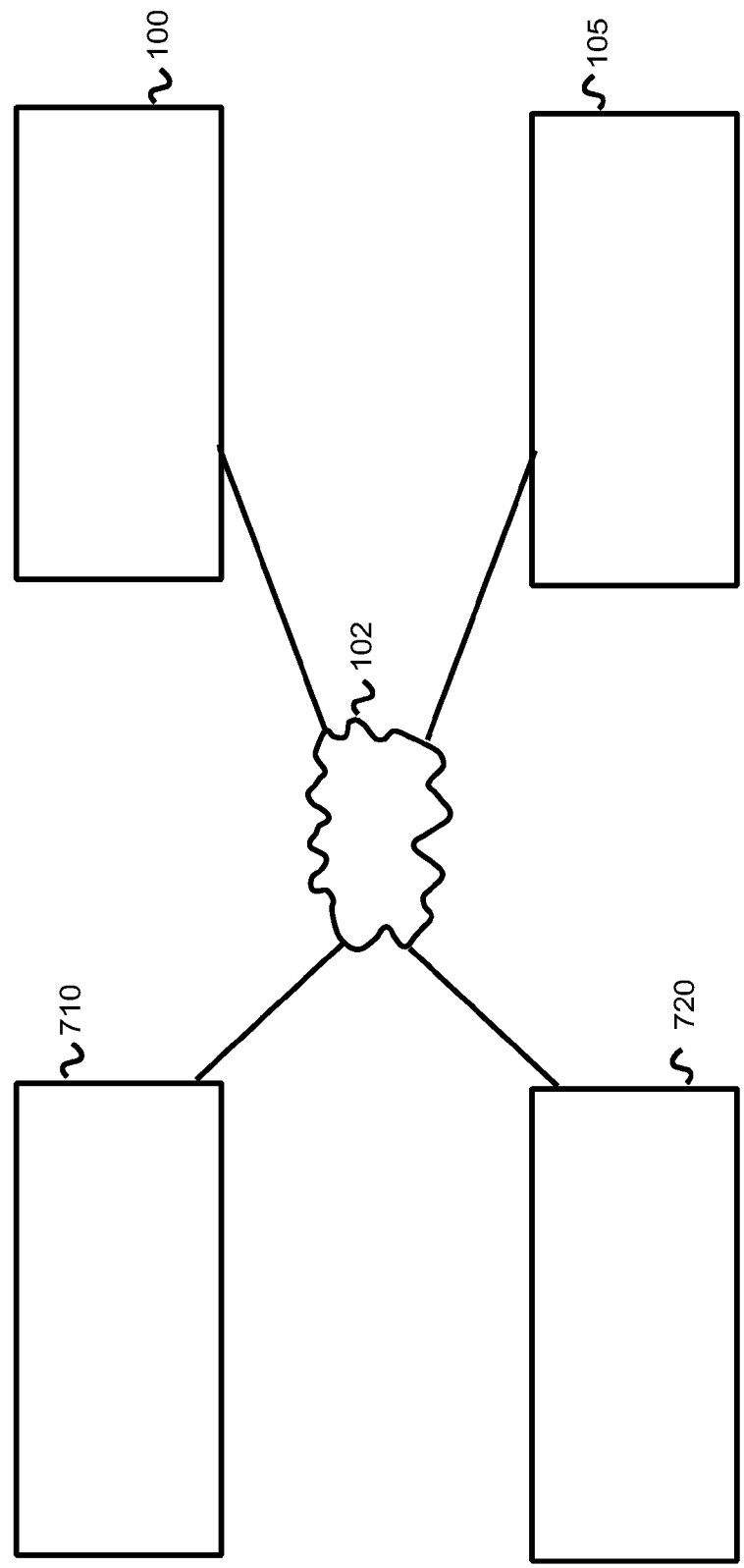

ONLINE PERSONAL LIBRARY

CROSS-REFERENCE TO RELATED APPLICATIONS

This application is a continuing application of application Ser. No. 09/634,725 filed Aug. 5, 2000 (now pending), which is a continuation-in-part application Ser. No. 09/478,796, filed on Jan. 7, 2000.

TECHNICAL FIELD

This invention is related in general to electronic information repositories, and in particular, to an online personal library.

BACKGROUND

The public interconnected computer networks—commonly called the Internet and colloquially called the web—have made possible a number of applications that were hitherto unthinkable. In general, a user visits web pages using a browser program executing on a client computer. When the user visits a web page, a document such as a news article, a downloadable file such as an e-book, downloadable software programs such as those available at www.shareware.com, a piece of music, a graphical image or other such object that is of interest, it may be a case that the user prefers to read or refer to the object at a later date. Currently the user has several choices—he can print the web page, download the page to his client computer, or make a book mark to enable an easy return to the web site for reference at a later date. But there are problems with each of these methods.

Printing every web page that is of interest quickly becomes unmanageable. A product called SurfSaver™ is a browser add-on, which lets a user to store Web pages directly from the browser into searchable folders on the user's client computer. While SurfSaver™ can be used to organize and search the information the user gathers on the Internet, it requires the user to download software to the client computer and create an information store for web pages downloaded to the client computer. But such downloading of web pages, documents, or files may consume significant resources on the client computer, and these downloaded web pages or files may not be readily available in a form that can be shared by others.

Book marking the web page or the location is a better solution than the above two methods. A typical bookmark comprises a location or address, usually specified in a Universal Resource Locator format, and a mnemonic so that the user remembers what information is stored at the location. In general, the browser program stores bookmarks in a special "book mark" file on the client computer. The location of this bookmark file is typically known to the browser, which loads the contents of the file and presents the bookmarks to the user when he makes an appropriate selection on the browser. Examples of such book marking methods are found in the commercially available browser programs such as Internet Explorer™, in which program the bookmarks are called "Favorites."

Often, it is the case that either the bookmarks are too many or they become "stale." Bookmarks become stale when a site to which the bookmark points no longer hosts the web page addressed by the bookmark. The user, who depended on the availability of the information online, is now left with a bookmark that does not point to useful data.

Additionally, sharing information with others either in a controlled manner or with a widespread audience is becoming an increasing need. Sharing information that is restricted as to the number of copies that can be made without infringing an author's or a publisher's rights is becoming important, There is a need, therefore, for a method and system to improve the state of the art to address these and other issues.

SUMMARY

The present invention is related to online repositories, which are described in U.S. patent application Ser. No. 09/478,796 filed Jan. 7, 2000, which disclosure is incorporated herein by reference in its entirety. A description of electronic message handling systems is provided in the Masters thesis by Naren Chaganti, "Integrating Electronic Message Handling Systems with Databases: A Security Perspective", submitted to the Faculty of Computer Science Engineering at The University of Texas at Arlington, Texas, May 1992, which is incorporated by reference in this disclosure in its entirety.

In one aspect, the present invention allows a user to create an online personal library for storage of digital items. As used in this application, an "item" or a "digital item" is any piece of analog or digital information such as a web page, data, a document such as a news article, word processor document, spread sheet, presentation, e-book, software programs, music, video, movie, a graphical image such as a photograph, a three-dimensional image, or a similar thing.

Two different roles for a person are envisioned to describe the principles of the present disclosure. They are: (1) a "user," who is a person or a computer program that creates or effectively "owns" the online personal library; and (2) a "requester", who is a person or a computer program that accesses the information stored in the personal library established by the user. Further, there is a service provider, which could be a person, a company or a computer program that establishes a server computer ("server") and allows users to use the server to create, maintain and operate the personal library. The service provider is not an essential entity to enable the principles of the present invention. The user and the requester may be the same entity, but performing different roles. Alternatively they could be separate entities.

The present invention is also directed toward a method and system for gathering, storing personal information on a server computer and releasing such information to authorized requesters. Several types of information are stored for release to different entities with appropriate authorization.

In one embodiment, the present invention is directed toward a method of for automatically disbursing personal information belonging to a user to a requester that is authorized by the user by transmitting said personal information from a server computer operated by a service provider, said server computer coupled to a database, the method comprising the steps of establishing an account for the user with the server computer; assigning an identifier to the user; entering personal information belonging to the user, said personal information comprising at least one of a plurality of information objects; assigning at least one of a plurality of security levels to each information object; storing in the database the user identifier, the information object and the security level assigned to the information object; receiving a request message from the requester, said request message comprising at least the user identifier; retrieving from the database the information object pertaining to the user identifier; securely transmitting the information object to the requester. In a further aspect, the invention comprises the steps of presenting an authorization by the requester; and verifying the requester's authorization.

Further, any modifications, updates, or changes are automatically notified to any authorized requesters. The requester optionally provides information about to whom and where to notify changes, such as address changes. Sending a message to an electronic mail box can accomplish such change notification function. In a preferred embodiment, a frequent unauthorized requester of information can be tagged as "junk" requester, to whom no further information will be released.

In another aspect of an embodiment, a user creates the online personal library on a server connected to a data communication network such as the Internet. In alternative embodiments, the user may subscribe to a service provided by an online service provider. In an embodiment, the user allocates a pre-determined amount of storage space on a storage device such as a hard disk. The user can increase this storage space as required. Alternatively, the server is preprogrammed to automatically increase the allocated space as the need arises, or after the user pays a subscription fee or a one-time fee for the space.

When such extra space is allocated, in one embodiment, the user is physically allocated the extra storage space for use to create or expand his library that could be accessed by requesters. In some embodiments, a program limiting the user to use only certain storage space is reprogrammed so that the user is allowed to use a larger space for the library. In one case, the user may control the way in which the library is created; requesters may merely use the library according to the schema established by the user. Alternatively, the user may allow a requester to alter the schema as well.

The storage space may be contiguous space in one physical device, or it could be distributed over a large number of physically separate disks that are accessible to the user over a network such as a Local Area Network, a Wide Area Network or a public data network. In case where the storage space is distributed over several physical devices, a controller—which could be a computer program—allows the user to access such distributed storage space in a transparent manner so that the user or requesters that access the library are unaware of the particular fashion in which the data are stored in a distributed manner over the network.

The library may be partitioned to have a number of directories and sub-directories, identified by labels or icons. The labels or icons may be implemented as hyper links. Each directory or sub-directory can be either visible or invisible, or can be separately protected by a password or other device. In order to establish this method of protection, the library schema advantageously uses a plurality of levels, at least one of the pluralities of levels to be allocated to each piece of data, at a fine granular level.

Once the user establishes a space to hold information, the server computer may assign an address—such as an Internet address in a dotted-decimal form or in an alphanumeric format, for example, http://library.serviceprovider.com or library@ serviceprovider.com—to the online library. This Internet address identifies the library to a user that subsequently accesses the library. The user then is allowed to upload digital items to the library from any computer such as his client computer. The user may direct a third party to transmit a digital item to the user's library by giving the third party his library's identifier. For example, the user may request a service such as e-books or other type of service by providing an identifier of the digital item, a destination address, which is a library address, an account name, and/or other required identifying or authorizing information such as a password if necessary. The user or the third party may then manually or via an automatic process send the digital item to the library via methods to transmit data such as E-mail, hyper text transfer protocol, file transfer protocol, Unix-to-Unix-Copy program (UUCP), or by dragging and dropping the digital item into the library.

When a requester's device accesses the server, the requester's device may first establish a connection, and make a request for a digital item stored in the library. This may happen by sending a packet of data containing a request message to the server. In one embodiment, the requester's identifying information is presented to the server in the packet or in a second packet. In response, the server may verify the requester's identification information against stored information in a database coupled to the server. Thereafter, the server may deliver the requested digital item to the requester's device, or any other device designated by the requester. In the case the digital item is delivered to a different device, the server may disconnect the requester's device, and thereafter establish a second connection with the designated device to deliver the requested digital item.

Depending on the security level of the requester, or security level of a password that the requester provides, or the type of address (such as an Internet address) of a device used by the requester, the time of day, the day of week, or other criterion established by the user, the requester is authorized to view or access a particular portion of the library. This authorization may enable the requester to perform a selection of such tasks as, in the case of a document, insert, delete or modify text, images or an audio clip, underline text, highlight or make margin notes with or without a digital signature, and the like, if the requester is permitted or authorized to do so. As stated above, the authorization can be separately provided or could be encoded in the type of password provided to the requester. Under this selective authorization scheme, a requester may be given only a subset of the available permissions to perform operations—i.e., the requester may be allowed only to view but not edit a document; only to add to but not delete from a video clip; only to make margin notes on a document but not change or underline the original text; make changes that are visible only to a select group of persons; and other similar tasks. When a requester edits a document, all other persons in the select group are automatically notified that a change has been made. In one embodiment, the changes are downloaded to the devices specified—if any—by the group. In other embodiments, the notified persons may subsequently access and retrieve the document to view or further edit the document, or provide a signature of approval or disapproval and store it in the library. In this manner, a document may be placed online, edited by one or more requesters, viewed or approved by others with secure digital signatures without the need to meet each other face-to-face.

The present invention may also be used to distribute information to a group of persons—either a closed subset of known persons or a larger audience on the network—without violating any copyright or other restrictions on items. Where an item is copyrighted, or otherwise restricted as to the number of requesters that can simultaneously use, or download the item, a locking mechanism is invented. As an example, if an item has a single-user license—such as the type of license one normally obtains by purchasing a book, a video tape, or a music CD—and if a first requester accesses the item from the library, the item is "locked" whereby subsequent requesters are prevented from using it. In this case, the requester is given a period of time in which to return the item, or a reminder is sent to the requester for returning the item after use. In other embodiments, the requester may check out the item for a predetermined time, for example, one day. The library will establish an expiration date on the item itself before the item is downloaded. Thus, when the requester attempts to use the item beyond the previously established time period, the item will not be accessible, since the usage period has expired. An embodiment uses a semaphore to establish this locking mechanism. Another embodiment uses a semaphore coupled with a digital counter that can be decremented with each requester access. Other embodiments are also possible.

In cases where a requester accesses an item that is restricted as to the number of simultaneous requesters, for a subsequent requester, the item will be shown as available in the library, but "checked out" by another requester. Further, a second requester may enlist his name or address in a "waiting list," indicating to the library that he preferred to be notified at the address when the item is released or checked in by the requester that is currently using the item. This method can be used to allow a few licenses purchased for a popular music or video item to be shared by a number of requesters by placing the licenses in a pool that can be accessed by a larger audience. In order to enable requesters to access multiple copies, a third-party user—i.e., one that is not the user that created the library—may "donate," "sell," "assign," or otherwise "contribute" his license to the library for a limited time or for an unlimited time. For example, a holder of a license can transmit his license code to the personal library, which license code can be stored in a license database coupled to the library, thereby allowing the library to provide access to as many persons as the licenses allow. In one embodiment, a license contributed by the third party user may expire after a predetermined time. In this case, a software process—such as a timer process—may be activated to periodically check for any expiration time and disable the enabled license.

Other methods of pooling licenses can be devised to share rights to use the restricted digital item. Suppose a digital item has a single-user license and is loaded to a third party user's personal computer. The third party user's computer is connected to a network or otherwise communicatively coupled to the server. When a requester wishes to access the restricted digital item, the server locks a copy of the item on the third party user's personal computer and allows the requester to use the digital item for a predetermined time. The server may accomplish this locking by downloading a plug-in, an applet or a client program to the client computer, which program establishes the lock either by making the license inaccessible to any other user, or by physically removing the license file from the client computer for the duration. Such license pooling method may include a method of locking copies of a restricted digital item distributed over the Internet.

Suppose a requester accesses the library using a device that is capable of retrieving and using a digital item without any need for further formatting, the digital item is downloaded to the device directly. When, on the other hand, a requester's device requires further formatting, software resident on the server computer or the device may initiate a handshaking protocol to establish the type of formatting required. For example, the requester's device may be capable of handling only a text-based interface, only a certain types of images such as only MPEG images, has a limited storage capability, or a limited viewing area. The requester's device may have other limitations on resources such as size and type of memory device; attached or attachable storage devices; input/output capability such as pointing device; voice recognition; text-to-speech capability; video input/output capability; numeric or alphanumeric keyboard; processing power; type of operating environment; whether or not a downloaded item can be locally executed; type of encryption/decryption; type of data communication or other protocol handled; file types; type and size of the viewing area or the like. In this case, the server determines the appropriate protocol that can be used and formats the digital item to fit the device that accesses the information. In an embodiment, the server formats the content appropriately to fit the requirements of the requester's device. To accomplish this, the server may have a formatter program that formats the digital item before downloading. In such cases, the server preferably has a database of required formats specified, and stored rules for formatting. In case a different data communication protocol is to be used to enable the requester device to access a requested digital item, the server may select an appropriate protocol translator—the server invokes the selected translator, inputs the digital item to the selected translator, and directs the output to the requester's device.

In other embodiments, for example, where the requester's device accesses the server to download the digital item for storage and later use, there may not be any need for preformatting by the server; the item can be downloaded and the requester may perform the translation locally at the client. The requester in this case may access the digital item from the server and translate it into a required local format after downloading an appropriate translator from either the server or a third-party supplier. In further alternative embodiments, the digital item may be delivered to the requester device via a streaming technique, by streaming video or audio to the device, if the requester device is suitably equipped.

BRIEF DESCRIPTION OF THE DRAWINGS

These and other objects, features and advantages of the present invention will be more readily understood in the following detailed description of the preferred embodiments and the appended claims with a reference to the drawings, where like numbers indicate like parts in the several views shown, and in which:

FIG. 4 illustrates a web page that allows a user to create an entry for an online library;

FIG. 5 depicts an example of the contents of a request message to add an item to an online library;

FIG. 7 shows an exemplary architecture of a number of computers engaged in license pooling.

DETAILED DESCRIPTION OF THE PREFERRED EMBODIMENTS

Figure 1:
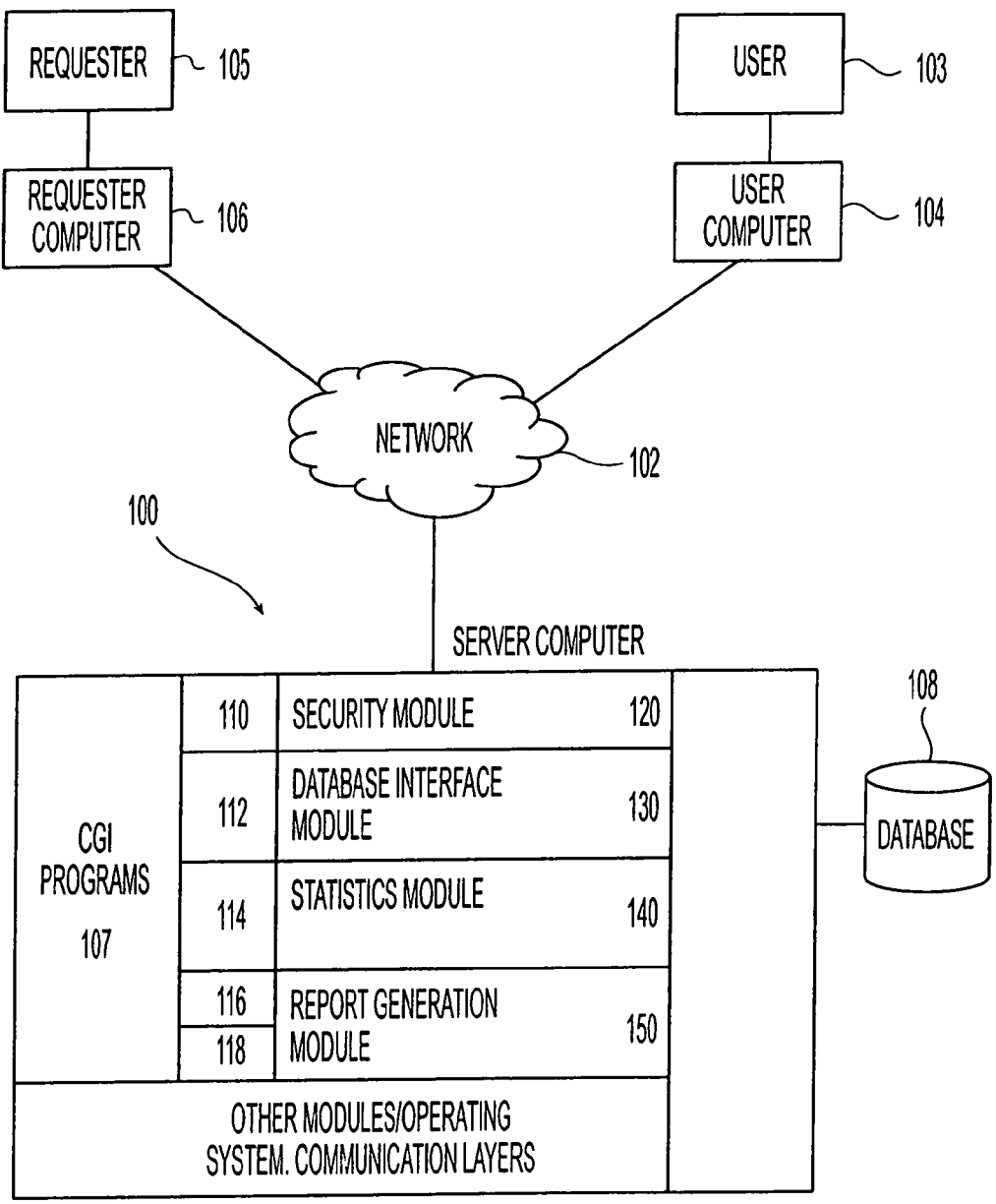
FIG. 1 depicts an architecture comprising a server computer 100, a user computer 104 and a requester computer 106 communicatively coupled to a communication network 102.

Referring to FIG. 1, a server computer 100 configured in accordance with the principles of the present invention is communicatively coupled to a communication network 102 such as the Internet. Also coupled to the communication network 102 is a user 103 operating a user computer 104 and a requester 105 operating a requester computer 106.

The server computer 100 illustratively comprises a microprocessor such as a Compaq® Alpha™ microprocessor, a disk drive, a memory such as a semiconductor memory, and runs an operating system such as Windows-NT™ or Linux. The server computer 100 is additionally equipped with a data communications device such as a 3-COM™ network card to connect to the network 102. In general, the connection to the network 102 can be established via an Internet Service Provider (ISP) or a direct connection. In a preferred embodiment, the server computer 100 is connected to the network 102 via a high-speed connection such as Digital Subscriber Line.

The server computer 100 is configured to function as a web server. The web server is typically a general purpose computer such as the server computer running software to interface with the Internet using sockets. Commercial suppliers such as Netscape Corporation of Sunnyvale, Calif. make available such web server software. Additionally, such web server software can also be downloaded and configured free of charge from some sources such as Apache.

Additional programs such as Common Gateway Interface (CGI) programs 107 reside on the server computer. The CGI programs 106 provide for communication and interaction between a user computer 104 and the server computer 100 via the network 102. These CGI programs 107, coupled with data communications software programs, are configured to receive packets of messages from computers connected to the network 102, decipher the information in the packets, and act according to instructions provided in the packets within the constraints imposed by an administrator managing the server computer 100.

In addition to performing the tasks of receiving and sending packets of data from and to the computers connected to the Internet, the CGI programs 107 are configured to perform other tasks such as communicate with a database 108 coupled to the server computer 100, and extract or store information in the database 108 according to the software instructions provided within the server computer 100 or in the packets received from the network 102. Persons skilled in the art can program these CGI programs 107 using programming tools and languages such as C, C++, Java, Perl and Shell scripts.

In an embodiment of the invention, the database 108 comprises a relational database management system, preferably, but not necessarily, with software code to enable Java Database Connectivity. Examples of such products include those marketed by the Oracle Corporation of Sunnyvale, Calif. It should additionally be noted that in an alternative embodiment the database 108 is not needed, or it could comprise software programs executing on the server computer 100.

The server computer 100 is configured to receive request messages from the user computer 104 over the internet in the Hyper Text Transfer Protocol (HTTP), File Transfer Protocol (FTP) or any similar protocol used to transfer data, video, voice or a combination of these media. After analyzing the request messages, the server computer 100 is configured to transmit in response messages that include "web pages" that are programmed in Hyper Text Markup Language (HTML) or a similar language.

Embedded in these web pages are components such as documents, scripts, objects, and frames that are configured to display colorful graphical images on a display device coupled to the user computer 104. Persons skilled in the art know how to make web pages using programming languages or tools such as HTML, Cold Fusion™, Java, Java Script™, Active Server Pages™ Dynamic HTML, the various markup languages such as Extensible Markup Language (XML), and similar others.

The user computer 104 is equipped with suitable devices and programs to connect to the network 102. In alternative embodiments, the user computer 104 is other device capable of establishing a communication in conjunction with other similar or dissimilar devices over a communication network such as the network 102. Examples of other commercially available digital interactive devices that are contemplated to function in place of the user computer 104 include a telephone, a WebTV™ device marketed by Microsoft Corporation of Redmond, Wash.; a Palm Pilot™ device marketed by 3-COM Corporation of Santa Clara, Calif., or other similar device; the device used in conjunction with the Wireless Web™ service from the Sprint Corporation of Westwood, Kans.; or a Wireless Access Protocol (WAP)-enabled device such as the device marketed by @Motion.com used in conjunction with Wireless Internet service provided by companies such as Phone.com and supported by protocols such as Wireless Markup Language, Mobile Phone Markup Language. Nokia, Motorola, Ericsson, and other companies manufacture such compatible wireless handset devices.

In one embodiment, the user computer 104 is a digital interactive device such as a personal computer comprising a processor similar to a Pentium-III™ microprocessor, a display device such as a flat panel display or a CRT, a memory such as semiconductor memory, a storage device such as a disk drive, an input device such as a keyboard, and a pointing device such as a mouse. In other embodiments, there could be provided a microphone or other speech input device and a voice or speech recognizer coupled to the user computer 104, whereupon a user 103 could provide input to the user computer 104 using spoken word commands. Currently, several commercial products are available—either hardware or software or a combination of both—that could be configured to perform speech or voice recognition of spoken words to perform several navigational functions with respect to the web. An example is the product Dragon Dictate™ marketed by Dragon Systems, Inc. of Newton, Mass. In the following, the word "selection" includes clicking a mouse or other pointing device coupled to the user computer 104 at least once; typing at least one character on a keyboard; allowing for a timer to expire; speaking at least one voice command into a microphone coupled to the user computer 104; or touching at least one area on a touch-sensitive screen and other equivalent methods.

In the embodiments described below, a user 103 can navigate the network 102 using either a graphical or a text-based navigational software. Additionally, in a preferred embodiment, the user computer 104 is configured to navigate the network 102 via a browser such as Internet Explorer™ marketed by Microsoft Corporation of Redmond, Wash., Opera™, available at—www.opera.com, a browser configured to enable viewing XML documents. Other browsers such as virtual reality browsers can be used to obtain a three dimensional experience of the network 102. An example of a text-based browser can be found in the software program Lynx, which is available free of charge.

The requester computer 106 comprises a processor such as a Pentium III microprocessor, a memory such as semiconductor memory, a storage device such as a hard drive, and optionally, a display device such as a CRT or an LCD display, a communications interface device such as a network card to enable connection to the network 102 either directly or via an Internet Service Provider. In alternative embodiments, the requester computer 106 could be a Java Chip enabled terminal device such as a printer directly coupled to the Internet using a protocol such as the Internet Printing Protocol, so that information objects could be directly downloaded and printed on the printer upon transmission by the server computer 100. Preferably, in such cases, there is equipped in the requester computer 106 such additional software as a handshake protocol to ensure a safe delivery of information objects.

In a preferred embodiment, the invention described herein is implemented principally on the server computer 100 and the user 103 interacts with the server computer 100 via a browser program executing on the user computer 104. Similarly, the requester 105 also interacts with the server computer 100 via the requester computer 106.

Gathering Updating and Storing Personal Information

Figure 2A:
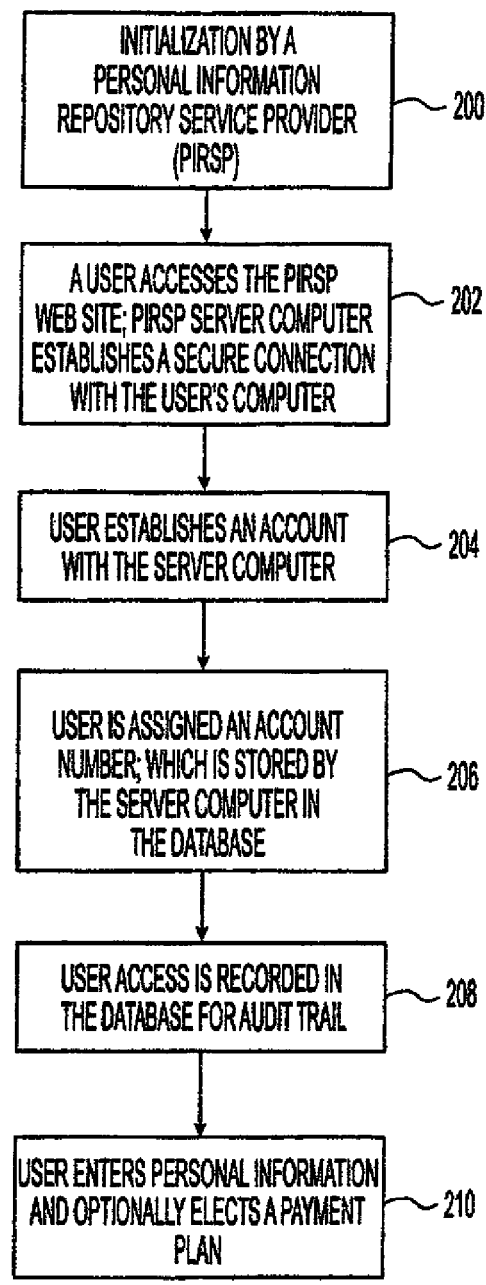
FIGS. 2A and 2B depict a flow chart of steps included in a preferred embodiment.
Figure 2B:
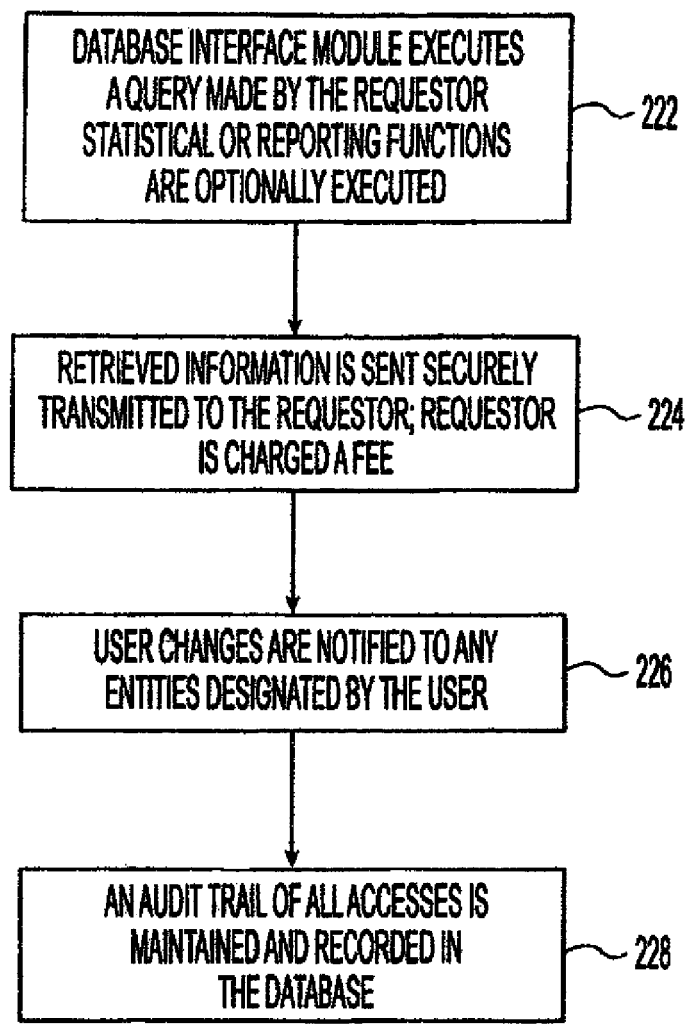

Referring to FIG. 2, the steps included in a preferred embodiment of the invented system are described. During an initialization step (step 200), in a preferred embodiment, a Personal Information Repository Service Provider (PIRSP) operates the server computer 100. In alternative embodiments, there is no service provider such as the PIRSP; and there are other methods of providing such service, such as establishing a personal web site for each user 103, said personal web site comprising information that can be accessed only by an authorized requester 105 in a secure manner; establishing a personal database coupled either directly to the Internet or accessible via the Internet or other communication network; or retrieving information stored elsewhere manually or in an automatic fashion.

Preferably, the PIRSP makes it known to a user 103 that it provides a trusted information repository service. In preferred and alternative embodiments, the PIRSP announces that its services are available free, or for a fee, and in the latter case, the fee is calculated based on a per transaction basis, or on a subscription basis, either from users that store information or from entities that request such information. Other embodiments comprise direct or vicarious payment methods for utilizing the services provided by the PIRSP. These payment methods include an agreement between the PIRSP and the user 103 to generate additional or alternative sources of revenue for the PIRSP via advertisements, referrals, introductions, chain marketing methods and the like.

In this application, any piece of information, however small in granularity or however agglomerated, is referred to as an "information object." Information objects can be implemented in an object-oriented manner, for example, each tuple or a field could be implemented as an object, a data structure or in any other manner known to persons skilled in the art.

Configuring the Database

In a preferred embodiment, the database 108 is a distributed database comprising several components (not shown) such as transaction manager, concurrency controller, memory manager, or a query optimizer. The database 108 is distributed over a large geographical area at several nodes, preferably by partitioning the tables and/or the tuples according to the needs of either the requesters or of the users in each node. The tables or the tuples can be partitioned either vertically or horizontally to enable fast and easy local access. In alternative embodiments, the database 108 is located at a single place.

In the following, a relational database model comprising sets of tuples, meta-data definitions for the tuples, and for other parts of the database organizational schema are described. It should be noted, however, that while a relational database model is described in the preferred embodiment, in alternative embodiments other methods of data definition, which are known to persons skilled in the art, are used. Preferably, the database 108 is configured to comprise a set of relations among several pieces of the user's personal information. These relations are shown in the following as tables according to the following schema. The schema for these tables can be designed by persons skilled in the art.

It should be noted that the user's social security number or alias can illustratively be used as primary keys to access the information from the tables. Other methods, such as date of birth, mother's maiden name, finger print scan, retina scan, or a combination of these methods can be used in other embodiments. The types of fields used in the illustration include Number [0-9], Character [A-Za-z0-9] and other special characters such as ASCII characters, and multimedia methods of storage for other types of data.

TABLE 1

Name and Address

| Field Name | Field Type | Field Length |
| --- | --- | --- |
| First Name | Character | 16 |
| Last Name | Character | 16 |
| Middle name/Initial | Character | 10 |
| Office Address | Character | 22 |
| Work Phone | Number | 10 |
| Mobile Phone | Number | 10 |
| Social Security Number* | Number | 9 |
| Mother's Maiden Name* | Character | 16 |

TABLE 2

Identity and Security

| Identity Type | Field Type | Field Length |
| --- | --- | --- |
| Social Security Number* | Number | 9 |
| Mother's Maiden Name* | Character | 16 |
| Password | Character | 16 |
| Password Reminder String | Character | 22 |
| E-mail address | Character | 22 |

The asterisk (*) indicates that the fields could form a primary key to the table. In a preferred embodiment, each field in each tuple is assigned a security classification, the details of which will be discussed below with reference to security. Referential integrity and Entity integrity of the information objects stored in these tables is preferably ensured. Tables can be joined according to well-known techniques such as inner and outer joins. Combining information objects from several tables can form views on tables. The tables, once formed are preferably normalized to make an efficient usage of the space.

Other tables, the schema for which are not described, are established to store information such as user's contact information (comprising home and work address, telephone and facsimile numbers, address of a nearest relative in case of an emergency, personal web home page address, personal web bookmarks, design of a portal); employment-related information (employer name, address, job title, job classification, salary range, supervisor's name and phone number, and the like); personal demographic information (sex, age, date of birth, marital status, spouse information); property-related information (own/rent home, amount of money in various bank accounts, ownership of stocks or other securities, property ownership information, personal property such as car, boat, private jet, and other details); health related information (types of medication currently used, surgeries undergone, type of drugs that tend to cause allergic reactions, smoking/drinking habits, hospitalization information, status of the several parts of the body, dental records, eye care information, genetic information, family medical history, etc); biometric information (retina scan, samples of speech, finger prints, DNA sequences, and other information); credit related information (mortgage payments, landlord/lender's name, address, phone number, credit card information and the like); personal preferences (movies, travel, books, frequent flier club memberships, important dates such as birthdays, anniversary dates, magazine subscriptions, etc); preferences such as choice of long-distance company, the features used in one's telephone service such as call waiting, call forwarding, three-way calling; names of friends and family members; travel preferences such as preferred airline, class of travel, whether an aisle or a window seat is preferred, whether a rental car is required, what size car is required; hotel preferences such as smoking/non-smoking section, any wake-up call is required, and if so, at what time, the type of amenities preferred or required at the hotel; pleasure-related preferences such as tee-time at a golf course, theater preferences, seat preferences, etc; or preferences for billing and payment methods (cash, credit/debit card, and the like). It should be noted that the type of information that can be stored in these tables can be unlimited. There is no requirement that all the pieces of information need to be furnished, since a requester 105 of information will be provided only that which is made available with the data base 130 or that which is authorized to be released to the requester 105.

A requester 105 that requests information also identifies himself and presents authorization from the user 103. Tables are also devised to store such requester's identification and authorization information for storage in the database 108. All accesses of information are recorded to generate a verifiable audit trail. Tables to store such audit information are designed in the database 108, preferably in a secure partition reachable only by persons with a very high security clearance.

Configuring the Server Computer

In a preferred embodiment, the server computer 100 is configured—in addition to being configured as a web server—to include a number of modules: a user account establishment module 610; a user account management module 112; a personal information collection module 114; a request reception module 116; an authorization verification module 118; a security module 120; a database interface module 130; a statistics module 140; and a report generation module 150. The server computer 100 preferably includes a trusted computer base (TCB) comprising a secure kernel, which includes the security module 120. Most of the security relevant code is stored in the secure kernel. All security relevant events are audited, recorded.

Further, events that signal any breach of security are defined and programmed. Upon the occurrence of such an event, an action, including sending an alarm to a predefined entity or person, is performed. Preferably, the modules are implemented as independent memory-resident processes—such as UNIX™ processes—capable of communicating with each other using interprocess communication facilities such as queues, semaphores, sockets, pipes, shared memory and the like. Persons skilled in the art can program these modules using programming languages and techniques such as C, C++, Java or Enterprise Java Beans. It should be noted that the number, nature and functionality of the modules described herein could be differently designed by other designers, and therefore should not be a limiting factor in construing the invention.

Figure 3:
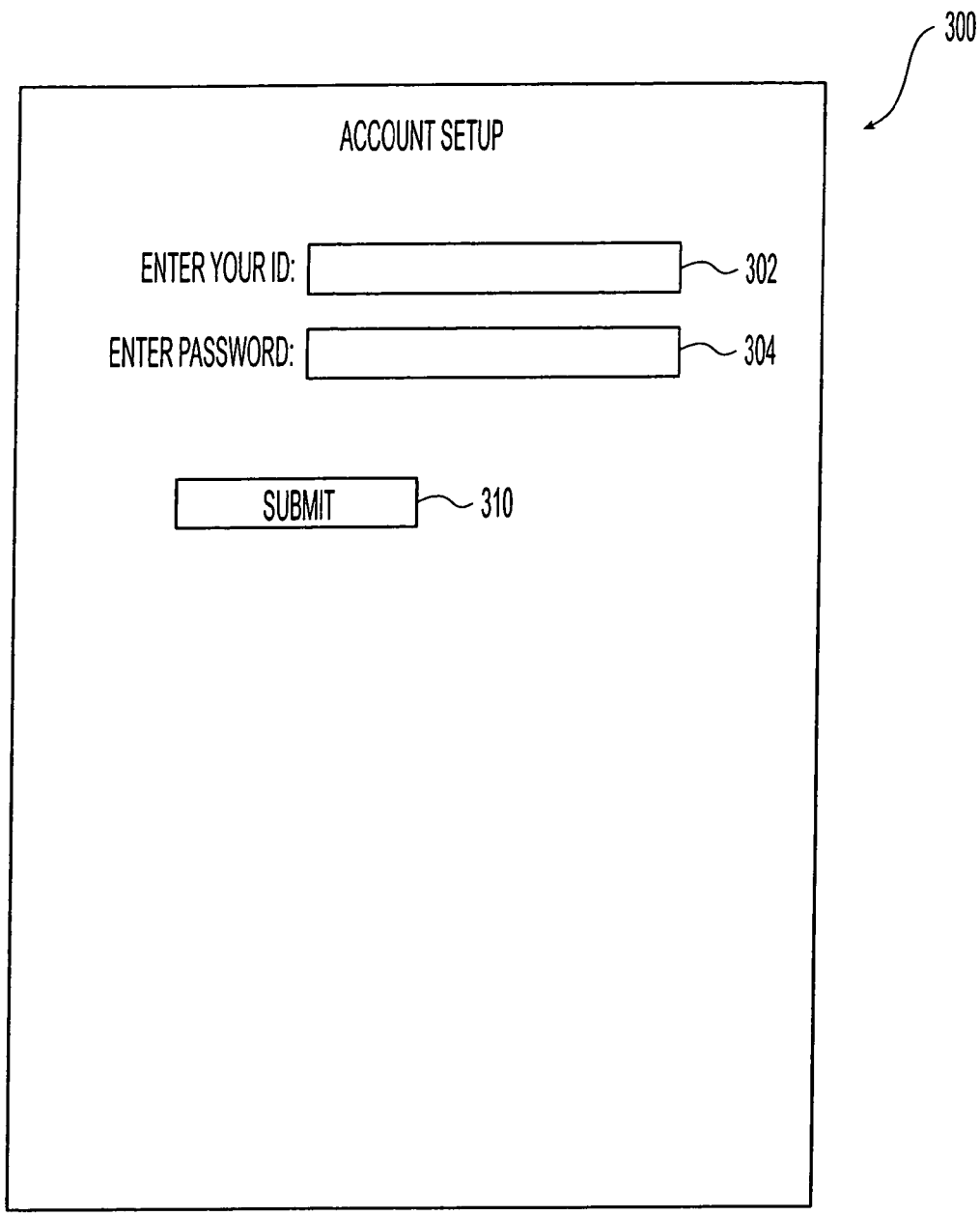
FIG. 3 is an illustrative web page for a user enrollment.

Referring to FIGS. 2 and 3, in a preferred embodiment, the user 103 accesses the PIRSP's web site whereupon the server computer 100 first establishes a secure connection with the user computer 104 (step 202).

The server computer 100 comprises at least one of a plurality of web pages such as the web page 300, which are displayed on the user computer 104. When the web page 300 is displayed, the user 103 is allowed to set up an account with the PIRSP, by entering his name or other identifier in a first text field 302, optionally entering a password string in a second text field 304 and selecting a push button 310 to transmit the web page 300 to the server computer 100 (step 204). In other embodiments, the user 103 provides information to the PIRSP, which information comprises a name, a billing address, a contact E-mail address.

The CGI programs 107 executing on the server computer 100 receive the web page 300, and invoke the user account establishment module 610 to create a new account for the user 103. This process includes allocating an account number to the user 103, which account number is preferably stored in the database 108 (step 206). In a preferred embodiment, the CGI programs 107 perform this process of receiving and transmitting packets of data during all interactions with the server computer 100. Therefore, in the following, this description is omitted.

The user account management module 112 comprises code configured to record every access of the user's personal information by the user 103 in the database 108. This establishes an audit trail for a subsequent use (step 208).

The user 103 thereafter enters his personal information such as the kind of information described before, by entering the information via text or other selections made in web pages displayed by the server computer 100 (step 210). It should be noted that since many areas of personal information can be stored by the user 103, it is not required that all such information be entered by the user 103 at one time. For example, the user 103 may initially wish to store his travel preferences and nothing else. This could be because he contemplates travel and wishes to provide this information to his travel agent. Later, the user 103 may enter his medical information and store it in appropriate tables since he wishes to visit his doctor. In this manner, at various times, the user 103 may furnish different aspects of personal information, which will be stored for a future use after it is entered once.

The user account management module additionally allows the user 103 to change or to update the user's password, address, telephone number or any other information. The user can change or update his personal information any time after the account is established. Preferably, the user can also provide a list of entities that should be notified for each change. In one embodiment, each information object that is changed or updated is notified to a list of authorized recipients automatically. In another embodiment, a change or an update is provided to a requester 105 when a request is made.

The user account management module 112 optionally allows the user 103 to select a payment plan for the services rendered by the PIRSP, block any request if the user 103 is in default of a payment, obtain credit card or other verification, and the like. In a preferred embodiment, the payment plans for the user 103 depend on the number of security classifications the user 103 has chosen, the number and nature of the information objects stored by the user 103, the number of requests for information received, the number of accesses or updates made by the user 103 to view and/or change the information objects, the type of customer service requested, the number of entities to which any changes are to be notified, the resources utilized by the user 103, or a combination of these and similar types of activities.

Preferably after user enrollment, the personal information collection module 114 obtains control of the program execution and presents the user 103 with at least one of a series of web pages. These web pages allow the user 103 to provide information to store in corresponding tables described above. In other embodiments, the user provides his information in a paper form, which is entered by the PIRSP into the database 108. Preferably, the user 103 also provides a security classification for each information object, at the tuple or at the field level, by selecting a radio button or a check box for each information object. In a preferred embodiment, there are a predetermined number of security classifications; in other embodiments, there could be a numerical value given to each class of security desired, and the higher the numerical value, the greater is the security classification. No security classification may imply that the information can be released freely to the requester 105, if the user's name is specified.

After the user 103 fills out the web page forms displayed on the client computer 100, the web pages are transmitted to the server computer 100, whereupon the CGI programs 107 receive, parse, and deliver portions of data to the database interface module 130 which stores portions of data entered by the user 103 as information objects in the database 108 in appropriate tables. In a preferred embodiment, the information objects that could be stored in a plurality of tables are collected from the user 103 in a single web page form. In other embodiments, each table or each part of a table can be separately populated with an information object or several objects retrieved from a single web page. In an alternative embodiment, the series of web pages can be displayed as framed or overlapping web pages and the user 103 preferably navigates from one page to another page by simply clicking on a predetermined area on a web page.

Preferably, the user 103 obtains from the server computer 100 at least one key to access his personal information. In one aspect, the key is provided to an authorized entity to enable access of the user's personal information stored in the database 108. There could be a number of types of authorization keys obtainable by the user: a one-time-use-only authorization key, a multiple use authorization key, a qualified authorization key, and others. In another aspect, the attributes encoded in the authorization key allow the release of a specific type of information from the server computer 100. Preferably, these encoded attributes of the authorization key—such as, how many times the authorization can be used to obtain access, what information is accessible using the authorization, any expiration time on the password, whether or not the trustworthiness of the requester is a precondition before releasing the information and the like.

In a preferred embodiment, the user 103 specifies these criteria and requests a key from the server computer 100. The key is preferably a string of alphanumeric characters of sufficient length as to prevent being deciphered easily by unscrupulous persons. In other embodiments, the authorization key is preferably encrypted, comprise a spoken word or phrase, a finger print scan, a retina scan, DNA identification, or other forms of identification. These keys could be used in a case such as when the user 103 is unconscious, and an immediate need exists to obtain medical or other information in order to save the patient.

In a preferred embodiment, the database interface module 130 comprises code to establish and verify security classification for each information object stored in the database. Preferably, for each information object, which could be a field, a row, a column, a tuple, or an entire table, a security classification is provided, which is marked on the object. This security classification is preferably an explicit and well-defined policy enforced by the security module 120. Individual accesses of each information object are recorded in the database 108. Each requester is clearly identified and an explicit audit trail for each access is recorded in the database 108. In another aspect, the database interface module 130 operates as a reference monitor as well. The reference monitor mediates all accesses of requests for information objects.

Other methods of ensuring security include establishing access control lists for each level of a multi-level security system; a system such as the Signed Document Markup Language (SDML); usage of trusted and known sources such as well-known companies as the requesters, public key encryption, third-party authentication, and other similar techniques.

In a preferred embodiment, potential requesters are also enrolled by the PIRSP in a similar manner as described for the user 103 (step 214). The server computer 100 establishes accounts for potential requesters, allocates identifiers, authenticates their trustworthiness and enables them to establish a payment plan for accessing information objects stored by the user 103. In one embodiment, where there are a number of users, statistical information, rather than individual pieces of information objects are offered for sale to potential requesters. In other embodiments, the potential requesters do not establish accounts with the PIRSP, and will pay as they go for each access of information as described below.

In an embodiment, the user 103 provides his identifier and a secure password, to a requester 105. This could be done, for example, when the user 103 decides to provide a travel agent or a tailor that his personal travel preferences or style and measurements can be obtained from the server computer 100 operated by the PIRSP. In one embodiment, the requester's web page (not shown) comprises an area, selecting which the user 103 can specie that his information can be obtained from the PIRSP's web site. Preferably, the user 103 provides his identifier, a specific authorization—for example to fetch the travel preferences or the medical history and nothing else—and requests the requester 105 to obtain his personal information from the PIRSP. The requester computer 106 is configured to receive this authorization over a secure channel, and to initiate a request to the PIRSP for the user's personal information.

In an alternative embodiment, the requester 105 requests the user 103 manually to fill out a form. This may happen in cases where the user 103 visits a doctor's office, or attempts to establish an appointment with the doctor's office. The doctor's office, which could be enrolled with the PIRSP, may request that the user 103 provide personal information via the PIRSP. The user 103 provides the requester 105 his identifier and authorization to obtain the information from the PIRSP.

Securely Disbursing Personal Information

In one embodiment, the PIRSP publicly discloses the database schema, so that any requester 105 can specify the type of information by naming the table and the fields that they want. In other embodiments, the actual database schema are kept secret, but the nature of information that is made available for access by a requester is announced to potential requesters.

The requester 105 preferably establishes a secure connection with the server computer 100 and presents the user's identifier and authorization to the server computer 100 (step 216).

Preferably, this process includes the following steps. First, a session with an encrypted Secure Socket Layer connection is established between the requester computer 106 and the server computer 100. Second, the requester 105 transmits at least one packet of data to the server computer 100, said packet of data comprising its identification, its electronic address (either dotted decimal form or other forms), any processor identifier of the requester computer 106. The server computer 100 receives these data and records them in the database 108 along with the time and date when the request is made. Third, the requester computer 106 is configured to present the user's identifier and authorization to the server computer. Alternatively, the requester 105 sends a secure electronic mail (E-mail) to the server computer 100. The secure Email contains a user identifier, a user-provided authorization key or password, and a request in the form of a database query.

In an alternative embodiment, the requester 105 can be the same as the user 103, such as in case the user 103 wishes to store information for himself, e.g., personal or business phone numbers, E-mail addresses, and other similar information typically stored in a person's wallet, frequent flier numbers, passwords to debit cards, preferences and the like. In this case, an authorization is not required for the user 103 to view information objects stored by him.

Preferably, after authenticating the requester 105, and if the requester 105 is determined to be a genuine entity, a security level is assigned to the requester's request (step 218). The security module 120 verifies the security classification for each field or information object requested before releasing it to the requester 105. Preferably, an information object is released to the requester only if the requester's security classification is at least that of the information object requested. Otherwise, the request is discarded and the attempt by the requester 105 is recorded as a failed request.

In a preferred embodiment, a requester that makes a predetermined number of unauthorized or failed requests is tagged as "junk" requester. The junk requester's identification information is stored in the database 108. A further request from this junk requester is ignored or an alarm message is generated to take an appropriate action (step 220).

The security module 120 preferably performs authentication and verification by assigning a numerical value to the requester 105. Any authorization from the user 103 presented by the requester 105 is also assigned a numerical value. Further, each information object that the requester 105 wishes to access from the server computer 100 is also assigned a numerical value.

Preferably, these numerical values represent a corresponding security level for each entity or item to which the value is assigned. In alternative embodiments, numerical values representing security levels are also assigned to the entities from where the request arrived at the server computer 100 such as the requester computer 106 and the network 102. The security module 120 thereafter examines the security levels of each entity included in the data transfer process (transaction) to determine the overall security level for the transaction. In a preferred embodiment, any requested information is released to a requester only if the security level of the requester 105 is at least that of all information objects requested. In other embodiments, only those information objects that are at or below the security level of the requester 105 are released to the requester.

In a preferred embodiment, the requester 105 formulates a query, in a readily executable form, preferably in a language such as the Structured Query Language. In other embodiments, the query by the requester 105 is a listing of the information objects requested. The database interface module 130 then executes at least one of a series of queries to extract the information sought by the requester 105 (step 222). The query optimizer included in the database 108 optimally retrieves the stored information after verifying the security level of the request, with the security level designated by the user 103 for an information object.

The security module 120 and the database interface module 130 use several alternative methods of accessing information. In one method, the database interface module 130 retrieves an information object if the security level of that information object is at or below the security level for the request and that of the authorization. In another embodiment, a data base view is automatically defined to extract all individually classified information objects, and in this case, if the security level of an information object is above the security level for the request, a blank entry is returned. Alternatively, the database interface module 130 may insert an indication instead of a blank entry, which indication specifies that either the information is not available, or it is available for a requester with a higher security level, and the like.

In another embodiment, the user 103 requests the PIRSP to disburse information to the requester 105 using an electronic means (step 224). In this case, the user is authenticated and the information objects are downloaded or transmitted to the requester 105, preferably via secure E-mail, file transfer protocol, after establishing a circuit-switched connection, facsimile, U.S. mail or any other method.

Preferably, the requester 105 is forbidden from reselling or retransmitting the information, or using it beyond an expiration date set either by the user 103 or by the PIRSP.

Preferably, to ensure this, information objects are copyrighted or otherwise contractually protected. Further, this could be a selling point to users, since the PIRSP not only guarantees the safety of the stored information, but in addition controls how this information is used.

In one embodiment, the requester 105 is charged a fee for receiving the information objects, on a per object basis, or on a subscription basis or for receiving statistical reports. The PIRSP may provide an incentive to the user 103 by paying the user 103 a portion of the fee to the user 103. In another embodiment, a requester may receive statistical report such as "how many male golf players between the ages 22 and 55 in the zip code 20006 are interested in trading stocks?" The statistics module 140 and report generation module 150 make appropriate queries in the database 108 and obtain the information. Preferably such statistical information is considered secure unless it has a tendency to reveal too much about the user's behavior. Thus, so long as information is aggregated and can remain anonymous, it may be released to potential requesters to assist marketing of products/services.

The user 103 may change or update his personal information. Examples of changes could be address or telephone number changes, and the like. Some changes are effective at a future date. Some information is updated either by the user 103 or by a third party (not shown).

An example of such updated information is medical information. When the user 103 makes the changes, he makes these by accessing the server computer 100 web site and entering his information as described above. The user 103 elects or designates any requesters or recipients of change notifications. The server computer 100 automatically retrieves the information objects that changed and notifies the designated requesters or recipients via secure E-mail, or other methods indicated above (step 226). In alternative embodiments, notification messages are left in mail boxes located on the server computer 100 and owned by requesters. Each change notification is recorded in the database 108 for audit trail purposes.

In a preferred embodiment, every time an information object is accessed, an entry is made into the database 108 and a secure audit trail established (step 228). This audit trail is preferably designed to track the activities of the PIRSP as well as the activities of the user 103 and the requester 105. This ensures that a clear audit is preserved to determine and prevent any misuse of personal information. Preferably such audit trail is established by programming in the secure kernel included in the server computer 100. All activities are stored in a specially partitioned area of the database 108 and are read-only after written by any process.

Creating an Online Personal Library

Referring now to FIG. 1, the computer architecture may also be used to implement an online personal library. As has been described above, two different roles for a person are envisioned to describe the principles of the present disclosure: (1) a "user," who is a person or a computer program that creates or effectively "owns" or controls the online personal library or a part of the library; and (2) a "requester", who is a person or a computer program that accesses the information stored in the personal library established by the user. Further, there is a service provider, which could be a person, a company or a computer program that establishes a server computer ("server") and allows users to use the server to create, maintain and operate the personal library. The service provider is not an essential entity to enable the principles of the present invention. The user and the requester may be the same entity, but performing different roles. Alternatively the service provider could establish the online library according to the principles described herein and allow requesters to access the items stored in the library. In another embodiment, the requester and the user could be separate entities.

In an embodiment, as described above, a user 103 (operating a user computer 104) establishes a connection with a data communication network 102. Then the user computer 104 establishes a link with the server 100 and creates an online personal library by utilizing a multilevel secure data storage and retrieval system such as the system described above. In alternative embodiments, the user 103 may subscribe to a service offered by a Library Service Provider (LSP) who operates the server 100. This can be accomplished by establishing an online account with the LSP in a manner similar to that described previously with reference to the PIRSP.

Table 3 depicts an example of a table schema that stores meta-information for the items stored in the library.

TABLE 3

Name and Address

| Field Name | Field Type | Field Length |
|---|---|---|
| User Name* | Character | 10 |
| User ID (if other than Name) | Character | 16 |
| Password | Character | 16 |
| File Name | Character | 22 |
| File Type | Character | 20 |
| Security Level | Number | 10 |
| Permissions List | Character | 20 |

In both the above cases, the user 103 is presented with a series of web pages using which the user 103 creates or allocates a pre-determined amount of storage space on the database 108 or a storage device coupled to the server 100. The library can be organized as a flat file, indexed file, a hierarchically organized file system, or a relational database.

When flat file architecture is used, the library is advantageously partitioned to have a number of directories and sub-directories, identified by labels or icons. The labels or icons are preferably implemented as hyperlinks. Each directory or sub-directory can be designed to be either visible or invisible, or can be separately protected by a password or other method. In order to establish this method of protection, the library schema advantageously uses a plurality of levels, at least one of the levels to be allocated to each piece of data, at a fine granular level. In an alternative embodiment, the user may control the way in which the library is created; requesters may merely use the library according to the schema established by the user.

Alternatively, the user 103 may grant permissions allowing a requester 105 to alter the schema as well. On the other hand, the library may be modeled in the form of a relational database, in which case, appropriate database schema are designed to create the library. Tables can be created to hold digital items that comprise the library. A different table can be advantageously used to hold a digital item of a particular type, for example, a table that holds all ASCII text items, a table that holds all Motion Pictures Expert Group (MPEG)-formatted items, and the like.

Other tables can be defined to hold access restrictions for a particular type of item, any permissions granted to a user or a requester, and the like. Alternative embodiments may include a hybrid type of items in a single table, which could be designed based on such other criteria as the type of restrictions imposed on a requester who wishes to access the item, and others.

Once the user 103 establishes a space to hold information, the server computer may assign an address—such as an Internet address in a dotted-decimal form or in an alphanumeric format, for example, http://library.serviceprovider.com or library@ serviceprovider.com—to the online library. This Internet address identifies the library to a user that subsequently accesses the library. The user 103 uploads digital items to the library from any computer such as his user computer 104.

Referring to FIG. 4, a sample web page 400 containing fields that a user 103 can specify to create catalogue information for items stored—or about to be stored—in the library. Such a catalogue allows the user 103 to search for the information. The catalogue information contains identification information for the file—such as the name of the author, its ISBN or Dewey Decimal Number, if any, year of publication, source where it is copied, and the like—in addition to the name of library 402 where it is stored, its overall security level 404, file type 406, permissions granted to different classes of users 408, and such other information. It should be noted that not all information may be necessary for an item to be stored in the library, and in some cases, where information is incomplete, default values can be assigned to security levels, file name and file types as determined by the LSP or a computer program. This catalogue information can be stored in the database 108 in a table such as Table 3.

The user may direct a third party to transmit a digital item to the user's library by giving the third party his library's identifier. For example, the user may request a service such as e-books or other type of service by providing an identifier of the digital item, a destination address, which is a library address, an account name, and/or other required identifying or authorizing information such as a password if necessary. The user or the third party may then manually or via an automatic process send the digital item to the library via methods to transmit data such as E-mail, remote copy program (rcp), hyper text transfer protocol (HTTP), file transfer protocol (ftp), Unix-to-Unix-Copy program (UUCP), cut-and paste, copy-and-paste, or drag-and-drop and the like.

Among the various methods of transmitting a digital item to be added to the library, E-mail, rcp, HTTP, ftp, and UUCP are well known to persons of ordinary skill in the art. Typically, in these methods, a user, (which could be a computer program or a person) initiates a connection from a first computer (such as a source where the digital item is stored) to a second computer (such as the server where the item is to be copied) by transmitting a Connection-Request message in accordance with an appropriate protocol such as the TCP/IP. Then, the source computer sends the digital item to the destination computer by either encapsulating the item in a packet or a series of packets depending on the method used. After a connection is established, there could be an exchange of a password that allows the source computer to access secure areas on the destination computer. These details are known to persons skilled in the art and do not need repetition here.

Referring now to FIG. 5, the contents of a request to add an item to the library by a user 103 are shown. In one embodiment, the request to add includes identification and classification information for the digital item. Further, if the item is not included as an attachment to the request to add message, a source from where the item is to be copied is also specified, along with any required password, authorization, or authentication information that is required to retrieve the digital item from the source and securely transmit and store it in the library.

Dragging and Dropping a Digital Item to the Library

Persons skilled in the art know some methods of implementing the copy-and-paste protocol or the drag-and-drop protocol. In the case of the drag-and-drop into the library, the user computer 104 and the server 100 may be coupled to homogenous or heterogeneous networks.

Further, suppose the user 103 is browsing a network 102 such as the Internet. The user 103 illustratively uses a browser program running on the user computer 104 to establish a connection with a first web site, for example, the web site http://www.pennar.com.

Figure 6:
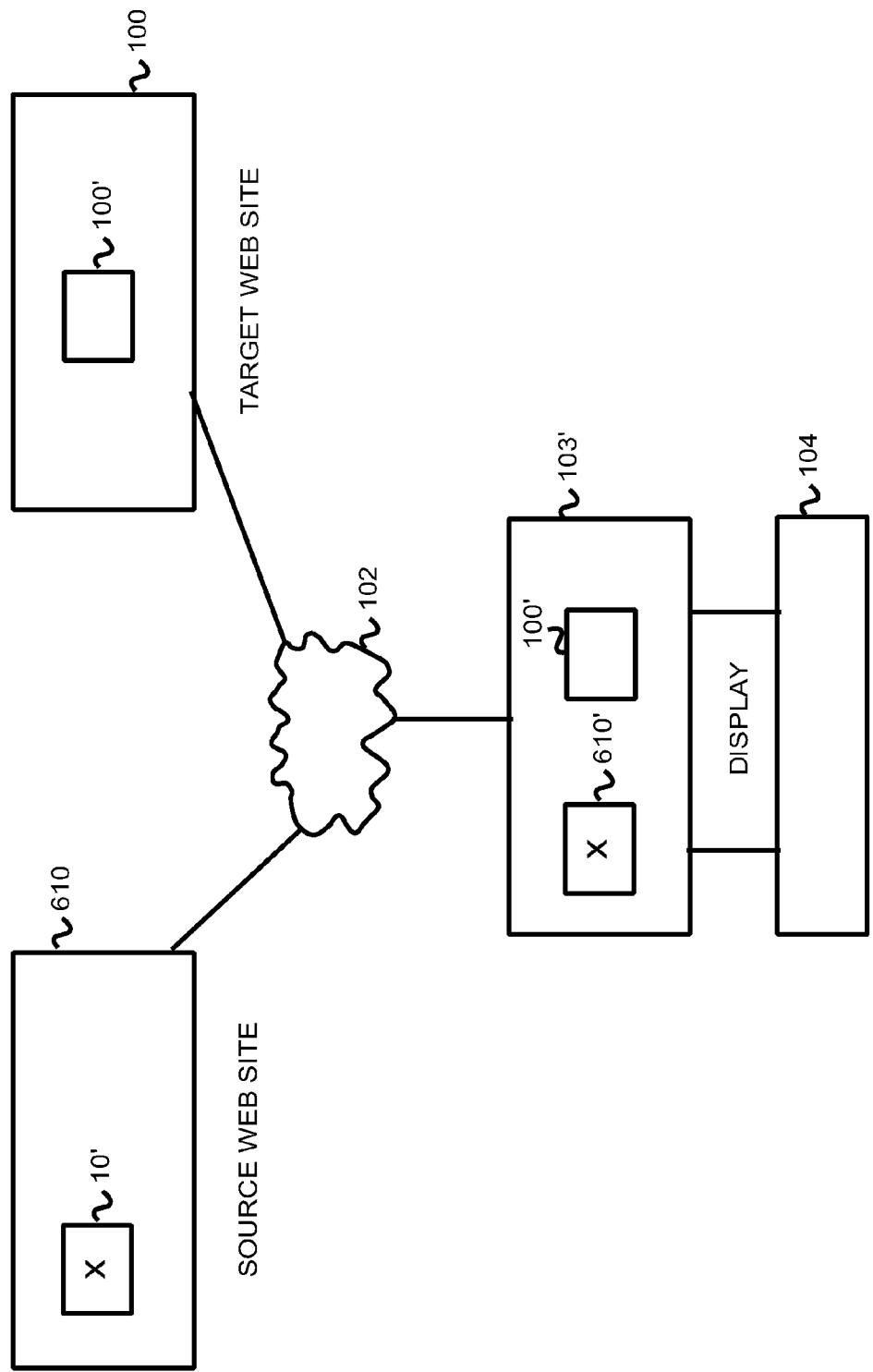
FIG. 6 is an architecture illustrating the act of dragging and dropping a digital item X from a source computer 610 to a target computer 100.

Referring now to FIG. 6, for the sake of illustration and not by way of limitation, we call the first computer the "source" computer 610 and the computer where the digital item is stored the target computer 100 (which is the server computer that has the library). Suppose that the user 103 wishes to store a web page 610' from the source computer 610 by copying the web page X to the target 100. By storing a copy of the web page X in the library, the user 103 may be able to access it at a later date, even if the page is deleted from the source computer 610. It should be noted that though the discussion herein is related to storing or transmitting a web page, the present invention is not limited only to storing web pages. Instead, the principles of the invention are applicable to any digital item or items.

As a preliminary step, the user computer 104 and the destination server are assumed to support the basic mechanism for the drag-and-drop protocol, which is preferably implemented using an event handler mechanism. To implement the drag-and-drop, the server 100 may download an event handler software program (not shown in FIG. 6) executable on the user computer 104. This event handler tracks events that are generated on the user computer 104. An event is an occurrence on a computer that generates an interrupt that can be handled by a program running on the computer such as the operating system, or by the processor. Events occur as a result of an action or inaction, such as the user does not respond to a request within a previously determined time period, causing a timeout event. Some common examples of events include mouse movements—mouse enter, mouse leave, button press, button release, button click, double click, key press, key release, and timeout. A programmer of ordinary skill in the art can define these events, the duration of time that constitutes a particular event, and events that can be ignored by the event handler. An event can be captured by software (running, for example on the user computer 104 or on the browser program). After an event is captured, the event handler program is invoked. The event handler takes the appropriate action, such as copying information into a buffer, and allowing the information to be pasted or transmitted to a destination. The source web site need not, but may, support the mechanism for drag-and-drop.

When the user 103 accesses the source, the user computer 104 may display a web page 610' or a link to the web page 610' on the user computer 104. The user 103 may make a selection—such as clicking a designated mouse button—to indicate that he wishes to transmit the information pointed by the browser to the library created on server 100. As shown in FIG. 6, in one embodiment, the user 103 may open two windows 610' and 100' on the user computer 104, and execute two browser program—one in each window. Then the user 103 navigates to an appropriate source location on window 610" to locate the digital item X of interest. The user 103 also navigates to an appropriate location on window 100' to identify an area in the library 100 at which he wishes to store a copy of the digital item X.

Then the user 103 executes an appropriate sequence of selections—which may include any combination of mouse button click, a key press, a voice command, or any other input method known to persons skilled in the art—to drag and drop, cut-and-paste, or copy-and-paste the digital item X from window 610' to the window 100'. As has been mentioned above, in alternative embodiments, the user may specify the address of the target computer 100 and accomplish transmittal of a copy of the digital item from source 610' to target 100 via E-mail, ftp, rcp, UUCP, HTTP or other methods.

When the item is dragged and dropped, appropriate events are generated on the user computer 104—such as when the user's mouse enters the area 610' on the user computer 104 display, when a button or a key is pressed while the mouse is within the area 610' and when the user continues to press the mouse or key while dragging the item, and when the user releases the mouse or key to drop the item on the window 100'. These events are captured, and handled by the event handler downloaded on the user computer 104 in conjunction with software on the target server 100. When the user drops the item on window 100', a secure connection—such as Secure Socket Layer or secure ftp—is opened with the server 100, any appropriate Authentication—such as password or other information—is provided, and the item is copied to the appropriate location for further viewing. In some cases, for example, with respect to the HTTP protocol, the digital item may be downloaded to a cache area on the user computer 104.

In this case, the act of dragging and dropping may advantageously copy the item from the user computer's 104 cache to the target 100. Where a user computer 104 is connected to the network 102 via an Internet Service Provider (ISP), the ISP may store the item in a cache at its location in a cache appliance—such as one manufactured by CacheFlow, Inc.,—for easy downloading by users. In such a case, the act of dragging and dropping (or copying and pasting) may be accomplished by opening a connection from the ISP cache appliance to the server 100 and transmitting the digital item to an appropriate location on the server 100 (target) after providing the user's account and password information.

Automatically Altering Library Storage Space

The user 103 can request the service provider to increase the library storage space as the need arises. This need can arise, for example, when the user attempts to add to the library an item that is larger than the available space. Similarly, when the user deletes a number of items storage space could be released, which can be reclaimed by the server 100 and this space could be added to either the space allocated to the user 103 or for any other use preferably after garbage collection. Suppose the user 103 inadvertently drags and drops an item to the library. If the item requires a storage space that should be allocated to the user, the item can be first stored in a temporary storage area on the server 100 or in the database 108. Then the server 100 executes an appropriate program to increase the storage space allocated to the user 103. To achieve an increase in the storage space, the service provider preferably executes an operating system function on the server 100 by providing it the user's identifier and his user privileges such as priority, security level, and others so that any newly allocated space is suitably configured to have the required security access level. This process can be performed either manually or automatically as the need arises to increase or decrease space, or after the user 103 pays a fee.

When such extra space is allocated, in one embodiment, the user is physically allocated the extra storage space for use to create or expand his library that could be accessed by requesters. In one embodiment, a program limiting the user to use only certain storage space is reprogrammed so that the user is allowed to use a larger space for the library.

The storage space may be contiguous space in one physical device, or it could be distributed over a large number of physically separate disks that are accessible to the user over a network such as a Local Area Network, a Wide Area Network or a public data network. In case where the storage space is distributed over several physical devices, a controller—which could be a computer program—allows the user to access such distributed storage space in a transparent manner so that the user or requesters that access the library are unaware of the particular fashion in which the data are stored in a distributed manner over the network.

Checking for Viruses

When an item is added or whenever any updates are made to a library, in one embodiment, the server computer 100 first makes sure that there is no attached or embedded virus present in the item. Searching the item looking for known virus signatures can accomplish this. Anti-virus programs are well known to persons skilled in the art. In some cases, the virus can be surgically removed from the item, and the item can be placed in the library. In other cases, a corrupted item may be discarded. In either case, an alerting message is sent to the user 103, notifying him of any virus detection, unless the user wishes not to receive such information. Any virus checking or detection is recorded in the database 108. Further, the source from where the corrupted item was obtained is recorded in the database 108 in a table of suspicious sources.

Subsequently, whenever a new item is added to the library, the source of the item is verified against an available list of suspicious sources in order to ensure authenticity and security of the data. Moreover, in order to maintain a current list of the latest viruses created by unscrupulous hackers, the library periodically scours trusted web sites or information sources to obtain information about new viruses, and download virus signatures, rules to identify viruses, and any anti-virus programs to the server 100 automatically to maintain an updated anti-virus mechanism.

Access the Library

The method by which a requester 105 accesses the online library includes the method described earlier with regard to the user's personal information with reference to FIG. 2, steps 200-228. These steps are applicable to disbursing information stored in the multi-level secure library similar to that of the user's personal information and are incorporated herein by reference. The LSP plays the role of a PIRSP. Additional details are described in the following. When a requester's device such as a requester computer 106 accesses the server 100, the requester's device 106 may first establish a connection with the server 100, and make a request o for a digital item stored in the library. Alternatively, a requester 105 may be presented with a mechanism—such as a web page—to search for an interested digital item by specifying its name or other identifying information. The requester computer 106 may do this by sending a packet of data containing a request message to the server 100. In one embodiment, the requester's identifying information is presented to the server 100 in the first packet or in a second packet. In response, the server 100 may verify the requester's identification information against stored information in a database coupled to the server 100. Thereafter, the server 100 may deliver the requested digital item to the requester's computer 100, or any other device designated by the requester 105. In the case where the digital item is delivered to a different device than the requester's computer 106 that requested the delivery, or in case where additional protection is deemed necessary, the server 100 may disconnect the requester's computer 106, and thereafter establish a second connection with the designated device to deliver the requested digital item.

Selective Access to the Requesters

Depending on the security level of the requester 105, or the security level of a password that the requester 105 provides, or the type or address (such as an Internet address) of a device used by the requester 105, the time of day, the day of week, or other criterion established by the user 103, a selective access is available to the requester 105. For example, only a particular portion of the library is visible or accessible to the requester 105. This selective access or authorization may enable the requester 105 to perform such tasks as, in the case of a document, insert, delete or modify text, images or an audio clip, underline text, highlight or make margin notes with or without a digital signature, and the like, if the requester 105 is permitted or authorized to do so. As stated above, the authorization can be separately provided or could be encoded in the type of password provided to the requester 105. Under this selective authorization scheme, a requester 105 may be given only a subset of the available permissions to perform operations—i.e., the requester 105 may be allowed only to view but not edit a document; only to add to but not delete from a video clip; only to make margin notes on a document but not change or underline the original text; make changes that are visible only to a select group of persons; and other similar tasks. When a requester 105 edits a document, all other persons in the select group are automatically notified that a change has been made. In one embodiment, the changes are downloaded to the devices specified—if any—by the group. In other embodiments, the notified persons may subsequently access and retrieve the document to view or further edit the document, or provide a digital signature of approval or disapproval and store it in the library. In this manner, a document may be placed online, edited by one or more requesters, viewed or approved by others with secure digital signatures without the need to meet each other face-to-face.

Restricting Access to a Predetermined Number of Simultaneous Requesters

The present invention may also be used to distribute information to a group of persons—either a closed subset of known persons or a larger audience on the network—without violating any copyright or other restrictions on items. Where an item is copyrighted, or otherwise restricted as to the number of requesters that can simultaneously use, or download the item, a locking mechanism is invented. As an example, if an item has a single-user license—such as the type of license one normally obtains by purchasing a book, a video tape, or a music CD—and if a first requester accesses the item from the library, the item is "locked" whereby subsequent requesters are prevented from using it. In this case, the requester is given a period of time in which to return the item, or a reminder is sent to the requester for returning the item after use. In other embodiments, the requester may check out the item for a predetermined time, for example, one day. The library will establish an expiration date on the item itself before the item is downloaded. Thus, when the requester attempts to use the item beyond the previously established time period, the item will not be accessible, since the usage period has expired. An embodiment uses a semaphore to establish this locking mechanism. Another embodiment uses a semaphore coupled with a digital counter that can be decremented with each requester access. Other embodiments are also possible.

In cases where a requester accesses an item that is restricted as to the number of simultaneous requesters, for a subsequent requester, the item will be shown as available in the library, but "checked out" by another requester. Further, a second requester may enlist his name or address in a "waiting list," indicating to the library that he preferred to be notified at the address when the item is released or checked in by the requester that is currently using the item.

This method can be used to allow a few licenses purchased for a popular music or video item to be shared by a number of requesters by placing the licenses in a pool that can be accessed by a larger audience.

License Pooling

In order to enable requesters to access multiple copies, a third-party user—i.e., one that is not the user that created the library—may "donate," "sell," "assign," or otherwise "contribute" his license to the library for a limited time or for an unlimited time. For example, a holder of a license can transmit his license code to the personal library, which license code can be stored in a license database coupled to the library, thereby allowing the library to provide access to as many requesters as the license allows. In one embodiment, a license contributed by the third party user may expire after a predetermined time. In this case, a software process—such as a timer process—may be activated to periodically check for any expiration time and disable license from further use. In further alternative embodiments, the digital item may be delivered to the requester device via a streaming technique, by streaming video or audio to the device, if the requester device is suitably equipped.

Referring now to FIG. 7, other methods of pooling licenses can be devised to share rights to use the restricted digital item. Suppose a digital item has a single-user license and is loaded to a third party user's personal computer 710. The third party user's computer is connected to network 102 or otherwise communicatively coupled to the server 100. The availability of the restricted item may be announced to potential requesters by listing it in a place visible to such requesters. Before or when a requester 105 wishes to access the restricted digital item, the server 100 locks a copy of the item on the third party user's personal computer 710 and allows the requester 105 to use the digital item for a predetermined time. The server may accomplish this locking by downloading a plug-in, an applet or a client program to the requester's computer 106, which program establishes the lock either by making the license inaccessible to any other requester, or by physically removing a file from the third party user's personal computer 710 for the duration. Such method of remote license provisioning may be expanded into a wide-area license pooling by locking copies of a restricted digital item across a number of computer 710, 720 and others distributed over the network 102.

Formatting the Digital Item for Delivery to a Designated Device

Suppose requester 105 accesses the library using a device 106 that is capable of retrieving and using a digital item without any need for further formatting. The digital item is downloaded to the requester's device 106 directly. When, on the other hand, a requester's device 106 requires further formatting—which could be evident from the type of the device as determined by the server 100 or by an explicit indication by the requester 105—software resident on the server or the requester's device 106 may initiate a handshaking protocol to establish the type of formatting required. For example, the requester's device 106 may be capable of handling only a text-based interface; only a certain types of images such as only MPEG images; has a limited storage capability; or a limited viewing area. The requester's device 106 may have other limitations on resources such as size and type of memory device; attached or attachable storage devices; input/output capability such as pointing device; voice recognition; text-to-speech capability; video input/output capability; numeric or alphanumeric keyboard; processing power; type of operating environment; whether or not a downloaded item can be locally executed; type of encryption/decryption; type of data communication or other protocol handled; file types; type and size of the viewing area or the like. In such cases, the server 100 formats the digital item to fit the device that accesses the information, or transmits the digital item using an appropriate protocol.

In an embodiment, the server 100 may format the content appropriately to fit the requirements of the requester's device 106. To accomplish this, the server 100 may execute a formatter program that formats the digital item appropriately before downloading. In such cases, the server 100 preferably has a database of required formats specified, and stored rules for formatting. On the other hand, the server 100 may alter, or remove certain portions of the item, such as attachments to an E-mail message.

In case a different data communication protocol is to be used to enable the requester device 106 to access a digital item, the server 100 may select an appropriate protocol translator; the server invokes the selected translator, inputs the digital item to the selected translator, and directs the output to the requester's device.

In other embodiments, for example, where the requester's device 106 accesses the server 106 to download the digital item for storage and later use, there may not be any need for preformatting by the server; the item can be downloaded or installed and the requester 105 may perform the translation locally at his device 106. The requester 105 may download or otherwise install the translator from either the server 100 or a third-party supplier.

The foregoing describes a method and a system for obtaining, storing and automatically disbursing personal information over a communications network. Though reference is made only to a single instance of each of the client and the server computers, it should be noted that the invention can be practiced using an architecture comprising a plurality of client computers (not shown) and/or a plurality of server computers (not shown). Additionally, though reference is made only to a single processor computer, the server or the client computer could comprise a distributed, parallel computing environment, either including a single-processor or a multiple-processor architecture, whether symmetric or asymmetric. In alternative embodiments, the user 103 operating the user computer 104 is thought to interact with the server computer 100 using a model such as that facilitated by the Java Bean, the Enterprise Java Bean or other similar technologies such as Remote Method Invocation, Distributed Component Object Model. Sessions could be implemented by using stateful or stateless Enterprise Java Beans and the like. The database 108 can be accessed via session or other kinds of beans, either a single instance of them or via numerous instances managed by another object layer. In alternative embodiments, the invention described herein can be implemented in part on the server computer 100 and in part on the user computer 104, in part as a servlet, as a downloaded JavaScript™ program, as a plugin program, as an applet, or any combinations thereof. In alternative embodiments, the server computer 100 is located behind a fire-wall, and may store a cookie, download a Dynamic HTML script, a JavaScript program or a plug-in program to the user computer 104 to achieve a portion of the functionality described herein. In one embodiment, no software is deposited on the user computer 104 other than the HTML page displayed on a browser. The word "network" comprises any heterogenous or homogenous collection of computer networks, public or private or a combination of both, which network includes intelligent or "passive" elements; either wholly or partly, and further includes routers, bridges and other transport mechanisms; executing a single protocol or a combination of a plurality of data communication protocols; effecting communication (transmission and/or reception) of information, which information comprises voice, video, data, and/or text or any combinations thereof using either in-band or out-of-band methods. The word "database" is assumed to comprise a flat file, an area in memory, an index file, a relational database, a sequential or a random access data storage and retrieval method operating in conjunction with any type of device, a distributed database or a single database, and could further comprise a relational database, hierarchical, sequential, random access or any other type of database, with or without a transaction manager, concurrency controller, memory manager, or a query optimizer. Further, the steps described herein are illustrative and not limiting, and the order of the steps described could be altered. Moreover, some of the steps could be collapsed into a single step, while some other steps are superfluous or optional and are described only to elaborate the principles of the invention. Persons skilled in the art may make modifications, rearrangements and adjustments to the disclosed preferred embodiments without undue experimentation or without significantly departing from the spirit and scope of the appended claims, which claims should be construed to include all these modifications, rearrangements, adjustments, and departures.

What is claimed is:

1. A server computer implemented method of online document collaboration by authorized users, the method comprising the following steps performed by a server computer system connected to the Internet:
    establishing an account for each of a plurality of users, wherein each account is associated with storage space to store one or more documents;
    storing a first document in the server computer system in a first account, the first document capable of being modified by a plurality of authorized users;
    enabling access to the first document via a browser-controlled window executing on a client computer by one or more authorized users;
    associating a set of restrictions with the first document, the restrictions including an ability to modify the first document in one or more permitted ways by one of a first group of users, the first group of users being users whose identities are known to the server computer system;
    receiving a request to access the first document from a first user, wherein the first user is a member of the first group of users, wherein the request to access accompanies the first user's identification information and authorization information;
    verifying the identity of the first user;
    if the first user is authorized to access the first document, then permitting the first user to access the first document via a first browser-controlled window executing on a client computer; and
    if the first user is authorized to modify the first document, then:
        (a) applying one or more modifications to the first document, the one or more modifications having been received from the first user;
        (b) electronically notifying one or more of a second group of users that the first user modified the first document, the second group of users being users whose identities are known to the server computer system; and
        (c) enabling a second user to further modify the first document, wherein the second user is a member of the second group of users who are notified of the one or more modifications made by the first user to the first document, and wherein the second user is not the same as the first user.

2. The server computer implemented method of claim 1, wherein the server computer system is capable of storing an indication of the one or more modifications made to the first document.

3. The server computer implemented method of claim 1, wherein the server computer system is capable of storing an indication that a notification has been sent to one or more of the second group of users that the first document is modified.

4. The server computer implemented method of claim 1, wherein the server computer system is capable of checking for viruses in the one or more modifications made to the first document.

5. The server computer implemented method of claim 1, wherein the server computer system is capable of altering storage space to accommodate modifications made to the first document.

6. The server computer implemented method of claim 1, wherein the server computer system is capable of verifying the first user based on:
    (a) information accessible using an authorization key presented by the first user;
    (b) expiration time for an authorization key presented by the first user;
    (c) security level of the first user as determined by the server computer system;
    (d) security level of a device used by the first user to access the server computer system;
    (e) type of device used by the first user to access the server computer system;
    (f) identity of device used by the first user to access the server computer system;
    (g) Internet address from which the first user accessed the server computer system;

(h) time of day when the first user accessed the server computer system; or (i) day of week when the first user accessed the server computer system.

7. The server computer implemented method of claim 1, wherein the server computer system is capable of storing the one or more modifications made to the first document by the first user such that the one or more modifications are visible only to a select group of users.

8. The server computer implemented method of claim 1, wherein the one or more modifications made to the first document includes adding material to the first document, deleting material from the first document, adding a digital signature to the first document, underlining material in the first document, or highlighting material in the first document.

9. The server computer implemented method of claim 1, wherein the one or more modifications to the first document are received from the first user via an out-of-band connection established between the server computer system and the client computer.

10. The server computer implemented method of claim 1, wherein the server computer system is capable of generating an alarm condition if the first user is not authorized to modify the first document.

11. The server computer implemented method of claim 1, wherein the server computer system is capable of formatting the first document in a manner suitable to the client computer.

12. The server computer implemented method of claim 1, wherein the server computer system is capable of receiving one or more features of the client computer, and sending the first document to the client computer after formatting the first document based on the one or more features of the client computer.

13. The server computer implemented method of claim 1, wherein the server computer system is capable of preventing the first document from being accessed by no more than a predetermined number of simultaneous users.

14. The server computer implemented method of claim 1, wherein if the first document is being used by a predetermined number of simultaneous users, the server computer system is capable of notifying a subsequent requester seeking access to the first document that the first document is unavailable for access at the time.

15. The server computer implemented method of claim 1, wherein upon relinquishment of access to the first document by a user, the server computer system is capable of notifying a requester waiting to access the first document that the first document has become available for access.

16. The server computer implemented method of claim 1, wherein first document is a word-processor document, a spread sheet, or a presentation.

17. A server computer system comprising:
one or more processors;
one or more memories coupled to the one or more processors;
one or more storage devices coupled to one or more processors, the one or more storage devices being capable of storing one or more documents;
a data communication device coupled to the one or more processors to establish a connection with one or more client computers via the Internet; and
one or more non-transitory computer-readable storage devices comprising processor-executable instructions, the processor-executable instructions capable of causing one or more processors to perform the following method steps:

establishing an account for each of a plurality of users, wherein each account is associated with storage space to store one or more documents;
storing a first document in the server computer system in a first account, the first document capable of being modified by a plurality of authorized users;
enabling access to the first document via a browser-controlled window executing on a client computer by one or more authorized users;
associating a set of restrictions with the first document, the restrictions including an ability to modify the first document in one or more permitted ways by one of a first group of users, the first group of users being users whose identities are known to the server computer system;
receiving a request to access the first document from a first user, wherein the first user is a member of the first group of users, wherein the request to access accompanies the first user's identification information and authorization information;
verifying the identity of the first user;
if the first user is authorized to access the first document, then permitting the first user to access the first document via a first browser-controlled window executing on a client computer; and
if the first user is authorized to modify the first document, then:
  (a) applying one or more modifications to the first document, the one or more modifications having been received from the first user;
  (b) electronically notifying one or more of a second group of users that the first user modified the first document, the second group of users being users whose identities are known to the server computer system; and
  (c) enabling a second user to further modify the first document, wherein the second user is a member of the second group of users who are notified of the one or more modifications made by the first user to the first document, and wherein the second user is not the same as the first user.

18. The server computer system of claim 17, wherein the server computer system is capable of storing an indication of the one or more modifications made to the first document.

19. The server computer system of claim 17, wherein the server computer system is capable of storing an indication that a notification has been sent to one or more of the second group of users that the first document is modified.

20. The server computer system of claim 17, wherein the server computer system is capable of checking for viruses in the one or more modifications made to the first document.

21. The server computer system of claim 17, wherein the server computer system is capable of altering storage space to accommodate modifications made to the first document.

22. The server computer system of claim 17, wherein the server computer system is capable of verifying the first user based on:
  (a) information accessible using an authorization key presented by the first user;
  (b) expiration time for an authorization key presented by the first user;
  (c) security level of the first user as determined by the server computer system;
  (d) security level of a device used by the first user to access the server computer system;
  (e) type of device used by the first user to access the server computer system;
  (f) identity of device used by the first user to access the server computer system;

(g) Internet address from which the first user accessed the server computer system;

(h) time of day when the first user accessed the server computer system; or (i) day of week when the first user accessed the server computer system.

23. The server computer system of claim 17, wherein the server computer system is capable of storing the one or more modifications made to the first document by the first user such that the one or more modifications are visible only to a select group of users.

24. The server computer system of claim 17, wherein the one or more modifications made to the first document includes adding material to the first document, deleting material from the first document, adding a digital signature to the first document, underlining material in the first document, or highlighting material in the first document.

25. The server computer system of claim 17, wherein the one or more modifications to the first document are received from the first user via an out-of-band connection established between the server computer system and the client computer.

26. The server computer system of claim 17, wherein the server computer system is capable of generating an alarm condition if the first user is not authorized to modify the first document.

27. The server computer system of claim 17, wherein the server computer system is capable of formatting the first document in a manner suitable to the client computer.

28. The server computer system of claim 17, wherein the server computer system is capable of receiving one or more features of the client computer, and sending the first document to the client computer after formatting the first document based on the one or more features of the client computer.

29. The server computer system of claim 17, wherein the server computer system is capable of preventing the first document from being accessed by no more than a predetermined number of simultaneous users.

30. The server computer system of claim 17, wherein if the first document is being used by a predetermined number of simultaneous users, the server computer system is capable of notifying a subsequent requester seeking access to the first document that the first document is unavailable for access at the time.

31. The server computer system of claim 17, wherein upon relinquishment of access to the first document by a user, the server computer system is capable of notifying a requester waiting to access the first document that the first document has become available for access.

32. The server computer system of claim 17, wherein first document is a word-processor document, a spread sheet, or a presentation.

33. An apparatus comprising:
one or more non-transitory computer-readable storage devices comprising processor- executable instructions, the processor-executable instructions capable of causing one or more processors of a server computer system to perform the following method steps:
establishing an account for each of a plurality of users, wherein each account is associated with storage space to store one or more documents;
storing a first document in the server computer system in a first account, the first document capable of being modified by a plurality of authorized users;
enabling access to the first document via a browser-controlled window executing on a client computer by one or more authorized users;
associating a set of restrictions with the first document, the restrictions including an ability to modify the first document in one or more permitted ways by one of a first group of users, the first group of users being users whose identities are known to the server computer system;
receiving a request to access the first document from a first user, wherein the first user is a member of the first group of users, wherein the request to access accompanies the first user's identification information and authorization information;
verifying the identity of the first user;
if the first user is authorized to access the first document, then permitting the first user to access the first document via a first browser-controlled window executing on a client computer; and
if the first user is authorized to modify the first document, then:
(a) applying one or more modifications to the first document, the one or more modifications having been received from the first user;
(b) electronically notifying one or more of a second group of users that the first user modified the first document, the second group of users being users whose identities are known to the server computer system; and
(c) enabling a second user to further modify the first document, wherein the second user is a member of the second group of users who are notified of the one or more modifications made by the first user to the first document, and wherein the second user is not the same as the first user.

34. The apparatus of claim 33, wherein the processor executable instructions include instructions to cause the server computer system to store an indication of the one or more modifications made to the first document.

35. The apparatus of claim 33, wherein the processor executable instructions include instructions to cause the server computer system to store an indication that a notification has been sent to one or more of the second group of users that the first document is modified.

36. The apparatus of claim 33, wherein the processor executable instructions include instructions to cause the server computer system to check for viruses in the one or more modifications made to the first document.

37. The apparatus of claim 33, wherein the processor executable instructions include instructions to cause the server computer system to alter storage space to accommodate modifications made to the first document.

38. The apparatus of claim 33, wherein the processor executable instructions include instructions to cause the server computer system to verify the first user based on:
(a) information accessible using an authorization key presented by the first user;
(b) expiration time for an authorization key presented by the first user;
(c) security level of the first user as determined by the server computer system;
(d) security level of a device used by the first user to access the server computer system;
(e) type of device used by the first user to access the server computer system;
(f) identity of device used by the first user to access the server computer system;
(g) Internet address from which the first user accessed the server computer system;
(h) time of day when the first user accessed the server computer system; or (i) day of week when the first user accessed the server computer system.

39. The apparatus of claim 33, wherein the processor executable instructions include instructions to cause the server computer system to store the one or more modifications made to the first document by the first user such that the one or more modifications are visible only to a select group of users.

40. The apparatus of claim 33, wherein the one or more modifications made to the first document includes adding material to the first document, deleting material from the first document, adding a digital signature to the first document, underlining material in the first document, or highlighting material in the first document.

41. The apparatus of claim 33, wherein the one or more modifications to the first document are received from the first user via an out-of-band connection established between the server computer system and the client computer.

42. The apparatus of claim 33, wherein the server computer system is capable of generating an alarm condition if the first user is not authorized to modify the first document.

43. The apparatus of claim 33, wherein the server computer system is capable of formatting the first document in a manner suitable to the client computer.

44. The apparatus of claim 33, wherein the processor executable instructions include instructions to cause the server computer system to receive one or more features of the client computer, and sending the first document to the client computer after formatting the first document based on the one or more features of the client computer.

45. The apparatus of claim 33, wherein the processor executable instructions include instructions to cause the server computer system to prevent the first document from being accessed by no more than a predetermined number of simultaneous users.

46. The apparatus of claim 33, wherein the processor executable instructions include instructions to cause the server computer system to notify a subsequent requester seeking access to the first document that the first document is unavailable for access at the time, if the first document is being accessed by a predetermined number of simultaneous users.

47. The apparatus of claim 33, wherein the processor executable instructions include instructions to cause the server computer system to notify a requester waiting to access the first documents that the first document has become available for access upon relinquishment of access to the first document by a user.

48. The apparatus of claim 33, wherein first document is a word-processor document, a spread sheet, or a presentation.

49. A computer implemented method of online document collaboration by authorized users, the method comprising the following steps performed by a client computer connected to the Internet:
   accessing a first document stored on a server computer system via a browser-controlled window executing on the client computer; and
   sending to the server computer system one or more modifications made to the first document, wherein the server computer system is capable of performing the following method steps:
   establishing an account for each of a plurality of users, wherein each account is associated with storage space to store one or more documents;
   storing a first document in the server computer system in a first account, the first document capable of being modified by a plurality of authorized users;
   enabling access to the first document via a browser-controlled window executing on a client computer by one or more authorized users;
   associating a set of restrictions with the first document, the restrictions including an ability to modify the first document in one or more permitted ways by one of a first group of users, the first group of users being users whose identities are known to the server computer system;
   receiving a request to access the first document from a first user, wherein the first user is a member of the first group of users, wherein the request to access accompanies the first user's identification information and authorization information;
   verifying the identity of the first user;
   if the first user is authorized to access the first document, then permitting the first user to access the first document via a first browser-controlled window executing on a client computer; and
   if the first user is authorized to modify the first document, then:
      (a) applying one or more modifications to the first document, the one or more modifications having been received from the first user;
      (b) electronically notifying one or more of a second group of users that the first user modified the first document, the second group of users being users whose identities are known to the server computer system; and
      (c) enabling a second user to further modify the first document, wherein the second user is a member of the second group of users who are notified of the one or more modifications made by the first user to the first document, and wherein the second user is not the same as the first user.

50. The computer implemented method of claim 49, wherein the server computer system is capable of receiving one or more features of the client computer, and sending the first document to the client computer after formatting the first document based on the one or more features received from the client computer.

51. The computer implemented method of claim 50, wherein the one or more features of the client computer includes viewing area of the client computer, type of the client computer, memory of the client computer, storage capability of the client computer or the type of a file the client computer is capable of handling.

52. A data storage system, comprising:
   one or more non-transitory computer data storage locations associated with each one of a plurality of identified users, the one or more storage locations capable of storing a document capable of being modified by one or more permitted users, said one or more permitted users being capable of accessing the modifiable document via browser-controlled window executing on a client computer, the client computer communicatively coupled to a server computer system,
   wherein the server computer system is capable of performing the following method steps:
   establishing an account for each of a plurality of users, wherein each account is associated with storage space to store one or more documents;
   storing a first document in the server computer system in a first account, the first document capable of being modified by a plurality of authorized users;
   enabling access to the first document via a browser-controlled window executing on a client computer by one or more authorized users;

associating a set of restrictions with the first document, the restrictions including an ability to modify the first document in one or more permitted ways by one of a first group of users, the first group of users being users whose identities are known to the server computer system;

receiving a request to access the first document from a first user, wherein the first user is a member of the first group of users, wherein the request to access accompanies the first user's identification information and authorization information;

verifying the identity of the first user;

if the first user is authorized to access the first document, then permitting the first user to access the first document via a first browser-controlled window executing on a client computer; and if the first user is authorized to modify the first document, then:
- (a) applying one or more modifications to the first document, the one or more modifications having been received from the first user;
- (b) electronically notifying one or more of a second group of users that the first user modified the first document, the second group of users being users whose identities are known to the server computer system; and
- (c) enabling a second user to further modify the first document, wherein the second user is a member of the second group of users who are notified of the one or more modifications made by the first user to the first document, and wherein the second user is not the same as the first user.

53. The data storage system of claim 52, wherein at least a portion of the information relating to the first document is associated with a security classification, and wherein access to the first document is permitted based on a classification given to the first user as compared to the security classification associated with the first document.

54. A server computer implemented method of online document collaboration by authorized users, the method comprising the following steps performed by the server computer system:

establishing an account for each of a plurality of users, wherein each account is associated with storage space to store one or more documents;

storing a first document in the server computer system in a first account, the first document capable of being modified by a plurality of authorized users;

enabling access to the first document via a browser-controlled window executing on a client computer by one or more authorized users;

associating a set of restrictions with the first document, the restrictions including an ability to modify the first document in one or more permitted ways by one of a first group of users, the first group of users being users whose identities are known to the server computer system;

receiving a request to access the first document from a first user, wherein the first user is a member of the first group of users, wherein the request to access accompanies the first user's identification information and authorization information;

verifying the identity of the first user;

if the first user is authorized to access the first document, then permitting the first user to access the first document via a first browser-controlled window executing on a client computer; and if the first user is authorized to modify the first document,
- (a) applying one or more modifications to the first document, the one or more modifications having been received from the first user;
- (b) electronically notifying one or more of a second group of users that the first user modified the first document, the second group of users being users whose identities are known to the server computer system; and
- (c) enabling a second user to approve or disapprove the one or more modifications made to the first document by the first user, wherein the second user is a member of the second group of users who are notified of the one or more modifications made by the first user to the first document, and wherein the second user is not the same as the first user.

55. The server computer implemented method of claim 54, wherein the server computer system is capable of storing an indication of the one or more modifications made to the first document.

56. The server computer implemented method of claim 54, wherein the server computer system is capable of storing an indication that a notification has been sent to one or more of the second group of users that the first document is modified.

57. The server computer implemented method of claim 54, wherein the server computer system is capable of checking for viruses in the one or more modifications made to the first document.

58. The server computer implemented method of claim 54, wherein the server computer system is capable of altering storage space to accommodate modifications made to the first document.

59. The server computer implemented method of claim 54, wherein the server computer system is capable of verifying the first user based on:
- (a) information accessible using an authorization key presented by the first user;
- (b) expiration time for an authorization key presented by the first user;
- (c) security level of the first user as determined by the server computer system;
- (d) security level of a device used by the first user to access the server computer system;
- (e) type of device used by the first user to access the server computer system;
- (f) identity of device used by the first user to access the server computer system;
- (g) Internet address from which the first user accessed the server computer system;
- (h) time of day when the first user accessed the server computer system; or (i) day of week when the first user accessed the server computer system.

60. The server computer implemented method of claim 54, wherein the server computer system is capable of storing the one or more modifications made to the first document by the first user such that the one or more modifications are visible only to a select group of users.

61. The server computer implemented method of claim 54, wherein the one or more modifications made to the first document includes adding material to the first document, deleting material from the first document, adding a digital signature to the first document, underlining material in the first document, or highlighting material in the first document.

62. The server computer implemented method of claim 54, wherein the one or more modifications to the first document are received from the first user via an out-of-band connection established between the server computer system and the client computer.

63. The server computer implemented method of claim 54, wherein the server computer system is capable of generating an alarm condition if the first user is not authorized to modify the first document.

64. The server computer implemented method of claim 54, wherein the server computer system is capable of formatting the first document in a manner suitable to the client computer.

65. The server computer implemented method of claim 54, wherein the server computer system is capable of receiving one or more features of the client computer, and sending the first document to the client computer after formatting the first document based on the one or more features of the client computer.

66. The server computer implemented method of claim 54, wherein the server computer system is capable of preventing the first document from being accessed by no more than a predetermined number of simultaneous users.

67. The server computer implemented method of claim 54, wherein if the first document is being used by a predetermined number of simultaneous users, the server computer system is capable of notifying a subsequent requester seeking access to the first document that the first document is unavailable for access at the time.

68. The server computer implemented method of claim 54, wherein upon relinquishment of access to the first document by a user, the server computer system is capable of notifying a requester waiting to access the first document that the first document has become available for access.

69. The server computer implemented method of claim 54, wherein first document is a word-processor document, a spread sheet, or a presentation.

70. A server computer system comprising:
one or more processors;
one or more memories coupled to the one or more processors;
one or more storage devices coupled to one or more processors, the one or more storage devices being capable of storing one or more documents;
a data communication device coupled to the one or more processors to establish a connection with one or more client computers via the Internet;
one or more non-transitory computer-readable storage devices comprising processor-executable instructions, the processor-executable instructions capable of causing the one or more processors to perform the following method steps:
establishing an account for each of a plurality of users, wherein each account is associated with storage space to store one or more documents;
storing a first document in the server computer system in a first account, the first document capable of being modified by a plurality of authorized users;
enabling access to the first document via a browser-controlled window executing on a client computer by one or more authorized users;
associating a set of restrictions with the first document, the restrictions including an ability to modify the first document in one or more permitted ways by one of a first group of users, the first group of users being users whose identities are known to the server computer system;
receiving a request to access the first document from a first user, wherein the first user is a member of the first group of users, wherein the request to access accompanies the first user's identification information and authorization information;
verifying the identity of the first user;
if the first user is authorized to access the first document, then permitting the first user to access the first document via a first browser-controlled window executing on a client computer; and
if the first user is authorized to modify the first document,
(a) applying one or more modifications to the first document, the one or more modifications having been received from the first user;
(b) electronically notifying one or more of a second group of users that the first user modified the first document, the second group of users being users whose identities are known to the server computer system; and
(c) enabling a second user to approve or disapprove the one or more modifications made to the first document by the first user, wherein the second user is a member of the second group of users who are notified of the one or more modifications made by the first user to the first document, and wherein the second user is not the same as the first user.

71. The server computer system of claim 70, wherein the server computer system is capable of storing an indication of the one or more modifications made to the first document.

72. The server computer system of claim 71, wherein the server computer system is capable of storing an indication that a notification has been sent to one or more of the second group of users that the first document is modified.

73. The server computer system of claim 71, wherein the server computer system is capable of checking for viruses in the one or more modifications made to the first document.

74. The server computer system of claim 71, wherein the server computer system is capable of altering storage space to accommodate modifications made to the first document.

75. The server computer system of claim 71, wherein the server computer system is capable of verifying the first user based on:
(a) information accessible using an authorization key presented by the first user;
(b) expiration time for an authorization key presented by the first user;
(c) security level of the first user as determined by the server computer system;
(d) security level of a device used by the first user to access the server computer system;
(e) type of device used by the first user to access the server computer system;
(f) identity of device used by the first user to access the server computer system;
(g) Internet address from which the first user accessed the server computer system;
(h) time of day when the first user accessed the server computer system; or
(i) day of week when the first user accessed the server computer system.

76. The server computer system of claim 71, wherein the server computer system is capable of storing the one or more modifications made to the first document by the first user such that the one or more modifications are visible only to a select group of users.

77. The server computer system of claim 71, wherein the one or more modifications made to the first document includes adding material to the first document, deleting material from the first document, adding a digital signature to the first document, underlining material in the first document, or highlighting material in the first document.

78. The server computer system of claim 71, wherein the one or more modifications to the first document are received from the first user via an out-of-band connection established between the server computer system and the client computer.

79. The server computer system of claim 71, wherein the server computer system is capable of generating an alarm condition if the first user is not authorized to modify the first document.

80. The server computer system of claim 71, wherein the server computer system is capable of formatting the first document in a manner suitable to the client computer.

81. The server computer system of claim 71, wherein the server computer system is capable of receiving one or more features of the client computer, and sending the first document to the client computer after formatting the first document based on the one or more features of the client computer.

82. The server computer system of claim 71, wherein the server computer system is capable of preventing the first document from being accessed by no more than a predetermined number of simultaneous users.

83. The server computer system of claim 71, wherein if the first document is being used by a predetermined number of simultaneous users, the server computer system is capable of notifying a subsequent requester seeking access to the first document that the first document is unavailable for access at the time.

84. The server computer system of claim 71, wherein upon relinquishment of access to the first document by a user, the server computer system is capable of notifying a requester waiting to access the first document that the first document has become available for access.

85. The server computer system of claim 71, wherein first document is a word-processor document, a spread sheet, or a presentation.

86. An apparatus comprising:
    establishing an account for each of a plurality of users, wherein each account is associated with storage space to store one or more documents;
    storing a first document in the server computer system in a first account, the first document capable of being modified by a plurality of authorized users;
    enabling access to the first document via a browser-controlled window executing on a client computer by one or more authorized users;
    associating a set of restrictions with the first document, the restrictions including an ability to modify the first document in one or more permitted ways by one of a first group of users, the first group of users being users whose identities are known to the server computer system;
    receiving a request to access the first document from a first user, wherein the first user is a member of the first group of users, wherein the request to access accompanies the first user's identification information and authorization information;
    verifying the identity of the first user;
    if the first user is authorized to access the first document, then permitting the first user to access the first document via a first browser-controlled window executing on a client computer; and
    if the first user is authorized to modify the first document,
        (a) applying one or more modifications to the first document, the one or more modifications having been received from the first user;
        (b) electronically notifying one or more of a second group of users that the first user modified the first document, the second group of users being users whose identities are known to the server computer system; and
        (c) enabling a second user to approve or disapprove the one or more modifications made to the first document by the first user, wherein the second user is a member of the second group of users who are notified of the one or more modifications made by the first user to the first document, and wherein the second user is not the same as the first user.

87. The apparatus of claim 86, wherein the processor executable instructions include instructions to cause the server computer system to store an indication of the one or more modifications made to the first document.

88. The apparatus of claim 86, wherein the processor executable instructions include instructions to cause the server computer system to store an indication that a notification has been sent to one or more of the second group of users that the first document is modified.

89. The apparatus of claim 86, wherein the processor executable instructions include instructions to cause the server computer system to check for viruses in the one or more modifications made to the first document.

90. The apparatus of claim 86, wherein the processor executable instructions include instructions to cause the server computer system to alter storage space to accommodate modifications made to the first document.

91. The apparatus of claim 86, wherein the processor executable instructions include instructions to cause the server computer system to verify the first user based on:
    (a) information accessible using an authorization key presented by the first user;
    (b) expiration time for an authorization key presented by the first user;
    (c) security level of the first user as determined by the server computer system;
    (d) security level of a device used by the first user to access the server computer system;
    (e) type of device used by the first user to access the server computer system;
    (f) identity of device used by the first user to access the server computer system;
    (g) Internet address from which the first user accessed the server computer system;
    (h) time of day when the first user accessed the server computer system; or
    (i) day of week when the first user accessed the server computer system.

92. The apparatus of claim 86, wherein the processor executable instructions include instructions to cause the server computer system to store the one or more modifications made to the first document by the first user such that the one or more modifications are visible only to a select group of users.

93. The apparatus of claim 86, wherein the one or more modifications made to the first document includes adding material to the first document, deleting material from the first document, adding a digital signature to the first document, underlining material in the first document, or highlighting material in the first document.

94. The apparatus of claim 86, wherein the one or more modifications to the first document are received from the first user via an out-of-band connection established between the server computer system and the client computer.

95. The apparatus of claim 86, wherein the server computer system is capable of generating an alarm condition if the first user is not authorized to modify the first document.

96. The apparatus of claim 86, wherein the server computer system is capable of formatting the first document in a manner suitable to the client computer.

97. The apparatus of claim 86, wherein the processor executable instructions include instructions to cause the server computer system to receive one or more features of the client computer, and sending the first document to the client computer after formatting the first document based on the one or more features of the client computer.

98. The apparatus of claim 86, wherein the processor executable instructions include instructions to cause the server computer system to prevent the first document from being accessed by no more than a predetermined number of simultaneous users.

99. The apparatus of claim 86, wherein the processor executable instructions include instructions to cause the server computer system to notify a subsequent requester seeking access to the first document that the first document is unavailable for access at the time, if the first document is being accessed by a predetermined number of simultaneous users.

100. The apparatus of claim 86, wherein the processor executable instructions include instructions to cause the server computer system to notify a requester waiting to access the first documents that the first document has become available for access upon relinquishment of access to the first document by a user.

101. The apparatus of claim 86, wherein first document is a word-processor document, a spread sheet, or a presentation.

102. A computer implemented method of online document collaboration by authorized users, the method comprising the following steps performed by a client computer connected to the Internet:
   accessing a first document stored on a server computer system via a browser-controlled window executing on the client computer; and
   sending to the server computer system one or more modifications made to the first document,
   wherein the server computer system is capable of performing the following method steps:
      establishing an account for each of a plurality of users, wherein each account is associated with storage space to store one or more documents;
      storing a first document in the server computer system in a first account, the first document capable of being modified by a plurality of authorized users;
      enabling access to the first document via a browser-controlled window executing on a client computer by one or more authorized users;
      associating a set of restrictions with the first document, the restrictions including an ability to modify the first document in one or more permitted ways by one of a first group of users, the first group of users being users whose identities are known to the server computer system;
      receiving a request to access the first document from a first user, wherein the first user is a member of the first group of users, wherein the request to access accompanies the first user's identification information and authorization information;
      verifying the identity of the first user;
      if the first user is authorized to access the first document, then permitting the first user to access the first document via a first browser-controlled window executing on a client computer; and
      if the first user is authorized to modify the first document,
         (a) applying one or more modifications to the first document, the one or more modifications having been received from the first user;
         (b) electronically notifying one or more of a second group of users that the first user modified the first document, the second group of users being users whose identities are known to the server computer system; and
         (c) enabling a second user to approve or disapprove the one or more modifications made to the first document by the first user, wherein the second user is a member of the second group of users who are notified of the one or more modifications made by the first user to the first document, and wherein the second user is not the same as the first.

103. The computer implemented method of claim 102, wherein the server computer system is capable of receiving one or more features of the client computer, and sending the first document to the client computer after formatting the first document based on the one or more features received from the client computer.

104. The computer implemented method of claim 103, wherein the one or more features of the client computer includes viewing area of the client computer, type of the client computer, memory of the client computer, storage capability of the client computer or the type of a file the client computer is capable of handling.

105. A data storage system, comprising:
   one or more non-transitory computer data storage locations associated with each one of a plurality of identified users, the one or more storage locations capable of storing a document capable of being modified by one or more permitted users, said one or more permitted users being capable of accessing the modifiable document via browser-controlled window executing on a client computer, the client computer communicatively coupled to a server computer system,
   wherein the server computer system is capable of performing the following method steps:
      establishing an account for each of a plurality of users, wherein each account is associated with storage space to store one or more documents;
      storing a first document in the server computer system in a first account, the first document capable of being modified by a plurality of authorized users;
      enabling access to the first document via a browser-controlled window executing on a client computer by one or more authorized users;
      associating a set of restrictions with the first document, the restrictions including an ability to modify the first document in one or more permitted ways by one of a first group of users, the first group of users being users whose identities are known to the server computer system;
      receiving a request to access the first document from a first user, wherein the first user is a member of the first group of users, wherein the request to access accompanies the first user's identification information and authorization information;
      verifying the identity of the first user;
      if the first user is authorized to access the first document, then permitting the first user to access the first document via a first browser-controlled window executing on a client computer; and
      if the first user is authorized to modify the first document,
         (a) applying one or more modifications to the first document, the one or more modifications having been received from the first user;
         (b) electronically notifying one or more of a second group of users that the first user modified the first document, the second group of users being users whose identities are known to the server computer system; and (c) enabling a second user to approve or disapprove the one or more modifications made to the first document by the first user, wherein the second user is a member of the second group of users who are notified of the one or more modifications made by the first user to the first document, and wherein the second user is not the same as the first user.

106. The data storage system of claim 105, wherein at least a portion of the information relating to the first document is associated with a security classification, and wherein access to the first document is permitted based on a classification given to the first user as compared to the security classification associated with the first document.

* * * * *